(12) United States Patent
Trees et al.

(10) Patent No.: US 8,875,405 B2
(45) Date of Patent: Nov. 4, 2014

(54) MICRO SURGICAL KNIFE WITH SAFETY FEATURE

(75) Inventors: Nick Quinton Trees, Riverside, CA (US); Norman Craig Delgado, La Verne, CA (US); Michael Hitoshi Ekinaka, Irvine, CA (US)

(73) Assignee: Oasis Medical, Inc., Glendora, CA (US)

( * ) Notice: Subject to any disclaimer, the term of this patent is extended or adjusted under 35 U.S.C. 154(b) by 0 days.

(21) Appl. No.: 13/451,345

(22) Filed: Apr. 19, 2012

(65) Prior Publication Data
US 2012/0215241 A1 Aug. 23, 2012

Related U.S. Application Data

(63) Continuation-in-part of application No. 12/872,339, filed on Aug. 31, 2010, now abandoned, which is a continuation-in-part of application No. 29/368,900, filed on Aug. 31, 2010, now Pat. No. Des. 639,432.

(60) Provisional application No. 61/322,784, filed on Apr. 9, 2010.

(51) Int. Cl.
*A61B 17/3211* (2006.01)
*A61F 9/013* (2006.01)

(52) U.S. Cl.
CPC ........... *A61F 9/0133* (2013.01); *A61B 17/3211* (2013.01); *A61B 2017/32113* (2013.01)
USPC ............................... 30/151; 30/162; 606/167

(58) Field of Classification Search
CPC .......... B26B 5/00; B26B 5/001; B26B 5/003; A61B 17/32; A61B 17/3211; A61B 17/3213
USPC ..................... 606/167; 30/162, 151; D24/147
See application file for complete search history.

(56) References Cited

U.S. PATENT DOCUMENTS

| | | | |
|---|---|---|---|
| 1,434,388 A | 11/1922 | Hughes | |
| D236,166 S | 7/1975 | Fishbein | |
| 3,905,101 A * | 9/1975 | Shepherd | 30/162 |
| 3,906,626 A * | 9/1975 | Riuli | 30/162 |
| D246,053 S | 10/1977 | Staub et al. | |
| D266,109 S | 9/1982 | Sertich et al. | |

(Continued)

FOREIGN PATENT DOCUMENTS

EP 1579815 A2 9/2005

OTHER PUBLICATIONS

European Search Report, Based On EP Application No. 11158330.8, Jul. 6, 2011, Munich.

(Continued)

*Primary Examiner* — Jason Daniel Prone
(74) *Attorney, Agent, or Firm* — Greenberg Traurig, LLP

(57) ABSTRACT

A surgical knife safety handle device comprises a handle body being essentially solid. A movable guard engages with the body for longitudinal movement between an extended position and a retracted position. The guard encloses a knife blade. The operation is an intuitive push/pull to extend or retract guard. The guard is formed of a clear material with a low profile that does not interfere with vision in use. The guard includes a leaf spring. The spring has a hemispherical protrusion on its underside that engages with a slot on the handle for positive engagement and an audible "click" when it seats.

8 Claims, 22 Drawing Sheets

(56) References Cited

U.S. PATENT DOCUMENTS

| | | | | |
|---|---|---|---|---|
| 4,414,974 | A | 11/1983 | Dotson et al. | |
| D277,507 | S | 2/1985 | Levy | |
| 4,523,379 | A * | 6/1985 | Osterhout et al. | 30/162 |
| 4,576,164 | A | 3/1986 | Richeson | |
| 4,790,312 | A | 12/1988 | Capuano, Sr. et al. | |
| 4,800,878 | A | 1/1989 | Cartmell | |
| 5,250,063 | A * | 10/1993 | Abidin et al. | 606/167 |
| 5,250,064 | A | 10/1993 | Schneider | |
| 5,275,606 | A * | 1/1994 | Abidin et al. | 606/167 |
| 5,292,329 | A * | 3/1994 | Werner | 606/167 |
| 5,330,492 | A * | 7/1994 | Haugen | 606/167 |
| 5,342,379 | A | 8/1994 | Volinsky | |
| 5,411,512 | A * | 5/1995 | Abidin et al. | 606/167 |
| 5,417,704 | A | 5/1995 | Wonderley | |
| 5,431,672 | A | 7/1995 | Cote et al. | |
| 5,496,340 | A * | 3/1996 | Abidin et al. | 606/167 |
| 5,527,329 | A | 6/1996 | Gharibian | |
| 5,578,050 | A | 11/1996 | Webb | |
| 5,584,816 | A | 12/1996 | Gyure et al. | |
| 5,620,454 | A * | 4/1997 | Pierce et al. | 606/167 |
| 5,662,669 | A | 9/1997 | Abidin et al. | |
| 5,665,099 | A | 9/1997 | Pilo et al. | |
| 5,683,407 | A | 11/1997 | Jolly et al. | |
| 5,741,289 | A | 4/1998 | Jolly et al. | |
| 5,752,968 | A | 5/1998 | Jolly et al. | |
| 5,779,724 | A | 7/1998 | Werner | |
| 5,792,162 | A | 8/1998 | Jolly et al. | |
| 5,827,309 | A | 10/1998 | Jolly et al. | |
| 5,843,107 | A | 12/1998 | Landis et al. | |
| 5,868,771 | A * | 2/1999 | Herbert et al. | 606/167 |
| 5,908,432 | A | 6/1999 | Pan | |
| 5,919,201 | A | 7/1999 | Carter et al. | |
| 5,924,206 | A | 7/1999 | Cote et al. | |
| 5,938,675 | A | 8/1999 | Gharibian | |
| 5,938,676 | A | 8/1999 | Cohn et al. | |
| 5,941,892 | A | 8/1999 | Cohn et al. | |
| D421,303 | S | 2/2000 | Cote et al. | |
| 6,022,364 | A | 2/2000 | Flumene et al. | |
| 6,053,929 | A * | 4/2000 | Cohn et al. | 606/167 |
| 6,077,283 | A | 6/2000 | Meyer et al. | |
| 6,233,832 | B1 * | 5/2001 | Berns | 30/162 |
| 6,391,041 | B1 | 5/2002 | Edens | |
| 6,416,524 | B1 | 7/2002 | Critz et al. | |
| D466,214 | S | 11/2002 | Otsuka | |
| 6,503,262 | B1 | 1/2003 | Edens | |
| D470,587 | S * | 2/2003 | Howell et al. | D24/147 |
| D470,938 | S * | 2/2003 | Howell et al. | D24/147 |
| D473,649 | S * | 4/2003 | Howell et al. | D24/147 |
| D475,135 | S | 5/2003 | Howell et al. | |
| 6,569,175 | B1 | 5/2003 | Robinson | |
| 6,623,499 | B1 | 9/2003 | Andreini et al. | |
| 6,626,925 | B2 * | 9/2003 | Newman et al. | 606/167 |
| 6,629,985 | B1 | 10/2003 | Kiehne | |
| D496,730 | S | 9/2004 | Morawski et al. | |
| D504,513 | S * | 4/2005 | Morawski et al. | D24/147 |
| 6,884,240 | B1 | 4/2005 | Dykes | |
| 6,979,340 | B2 * | 12/2005 | Bilenski et al. | 606/167 |
| 7,022,128 | B2 | 4/2006 | Morawski et al. | |
| 7,055,248 | B2 | 6/2006 | Cote | |
| 7,087,067 | B2 | 8/2006 | Kehr et al. | |
| 7,153,317 | B2 * | 12/2006 | Kanodia et al. | 606/167 |
| D535,026 | S * | 1/2007 | Griffin et al. | D24/147 |
| D537,528 | S | 2/2007 | Christensen et al. | |
| 7,207,999 | B2 | 4/2007 | Griffin et al. | |
| D561,898 | S * | 2/2008 | Goto | D24/147 |
| 7,346,989 | B2 | 3/2008 | Shi | |
| D571,010 | S | 6/2008 | Cote | |
| 7,387,637 | B2 | 6/2008 | Morawski et al. | |
| D575,403 | S | 8/2008 | Endo | |
| D581,239 | S | 11/2008 | Gibbs | |
| 7,485,126 | B2 | 2/2009 | Adelman et al. | |
| 7,491,177 | B2 | 2/2009 | Hibner | |
| D619,251 | S | 7/2010 | Justiniano-Garcia et al. | |
| 7,901,422 | B2 | 3/2011 | Morawski et al. | |
| 7,905,894 | B2 | 3/2011 | Morawski et al. | |
| 7,909,840 | B2 | 3/2011 | Cote et al. | |
| D639,432 | S | 6/2011 | Trees et al. | |
| D642,682 | S | 8/2011 | Chaudhary et al. | |
| 8,114,103 | B2 * | 2/2012 | Rasco | 606/167 |
| 8,156,653 | B2 * | 4/2012 | Austria et al. | 30/162 |
| 8,205,340 | B2 * | 6/2012 | Austria et al. | 30/162 |
| 8,256,330 | B2 * | 9/2012 | Auchter et al. | 30/151 |
| 8,256,331 | B2 * | 9/2012 | Auchter et al. | 606/167 |
| D685,091 | S * | 6/2013 | Morawski et al. | D24/147 |
| D685,092 | S * | 6/2013 | Morawski et al. | D24/147 |
| 8,464,430 | B2 * | 6/2013 | Cote | 30/162 |
| 8,578,613 | B2 * | 11/2013 | Nallakrishnan | 30/151 |
| 2002/0124418 | A1 * | 9/2002 | Votolato | 30/294 |
| 2002/0143352 | A1 | 10/2002 | Newman et al. | |
| 2003/0093100 | A1 * | 5/2003 | Robinson | 606/167 |
| 2004/0181247 | A1 * | 9/2004 | Kehr et al. | 606/167 |
| 2004/0236359 | A1 * | 11/2004 | Shi | 606/167 |
| 2005/0065541 | A1 * | 3/2005 | Abidin et al. | 606/167 |
| 2005/0119680 | A1 * | 6/2005 | Dykes | 606/167 |
| 2006/0085019 | A1 | 4/2006 | Cote et al. | |
| 2007/0255298 | A1 * | 11/2007 | Djordjevic et al. | 606/167 |
| 2007/0265651 | A1 * | 11/2007 | Yi et al. | 606/167 |
| 2008/0058843 | A1 | 3/2008 | Morawski et al. | |
| 2008/0319463 | A1 | 12/2008 | Hickingbotham | |
| 2009/0151168 | A1 * | 6/2009 | Dadam | 30/162 |
| 2009/0204135 | A1 | 8/2009 | Cote | |
| 2010/0137894 | A1 * | 6/2010 | Ueno et al. | 606/167 |
| 2010/0146799 | A1 * | 6/2010 | Hoffman et al. | 606/167 |
| 2010/0228274 | A1 * | 9/2010 | Baid | 606/167 |
| 2011/0092995 | A1 * | 4/2011 | Cote et al. | 606/167 |
| 2011/0092996 | A1 * | 4/2011 | Morawski et al. | 606/167 |
| 2011/0098734 | A1 * | 4/2011 | Cote | 606/167 |
| 2011/0251631 | A1 * | 10/2011 | Trees et al. | 606/167 |
| 2012/0083816 | A1 * | 4/2012 | Hajgato et al. | 606/170 |
| 2013/0079804 | A1 * | 3/2013 | Milton et al. | 606/167 |
| 2013/0204284 | A1 * | 8/2013 | Morawski et al. | 606/167 |

OTHER PUBLICATIONS

Oasis Medical Inc., "Oasis Premier Shield Safety Scalpels", Oasis Product Catalog, 2006, Glendora, California.

PCT/US13/36559 International Search Report and Written Opinion, mailed May 3, 2013 from the International Search Authority/United States.

* cited by examiner

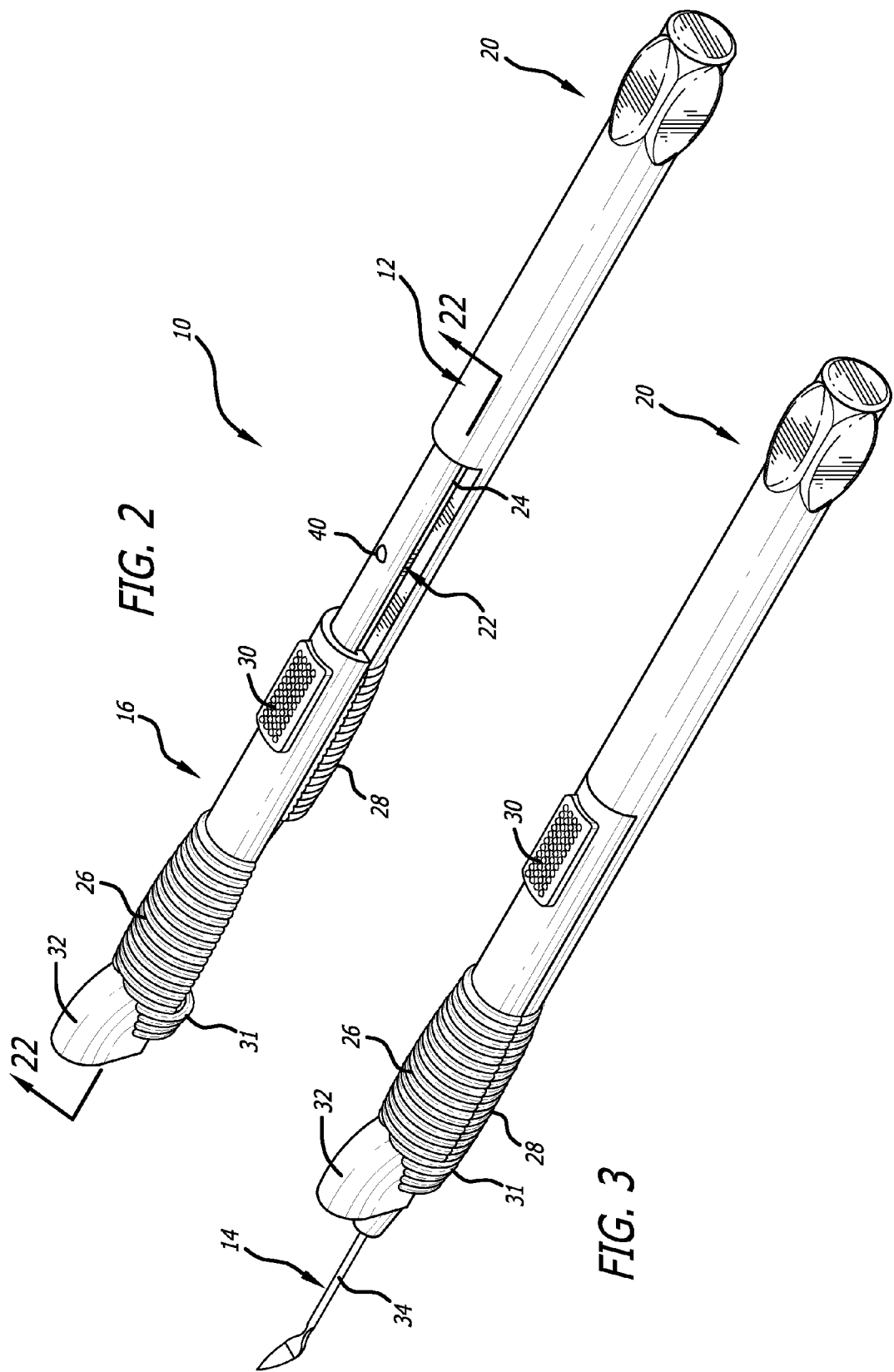

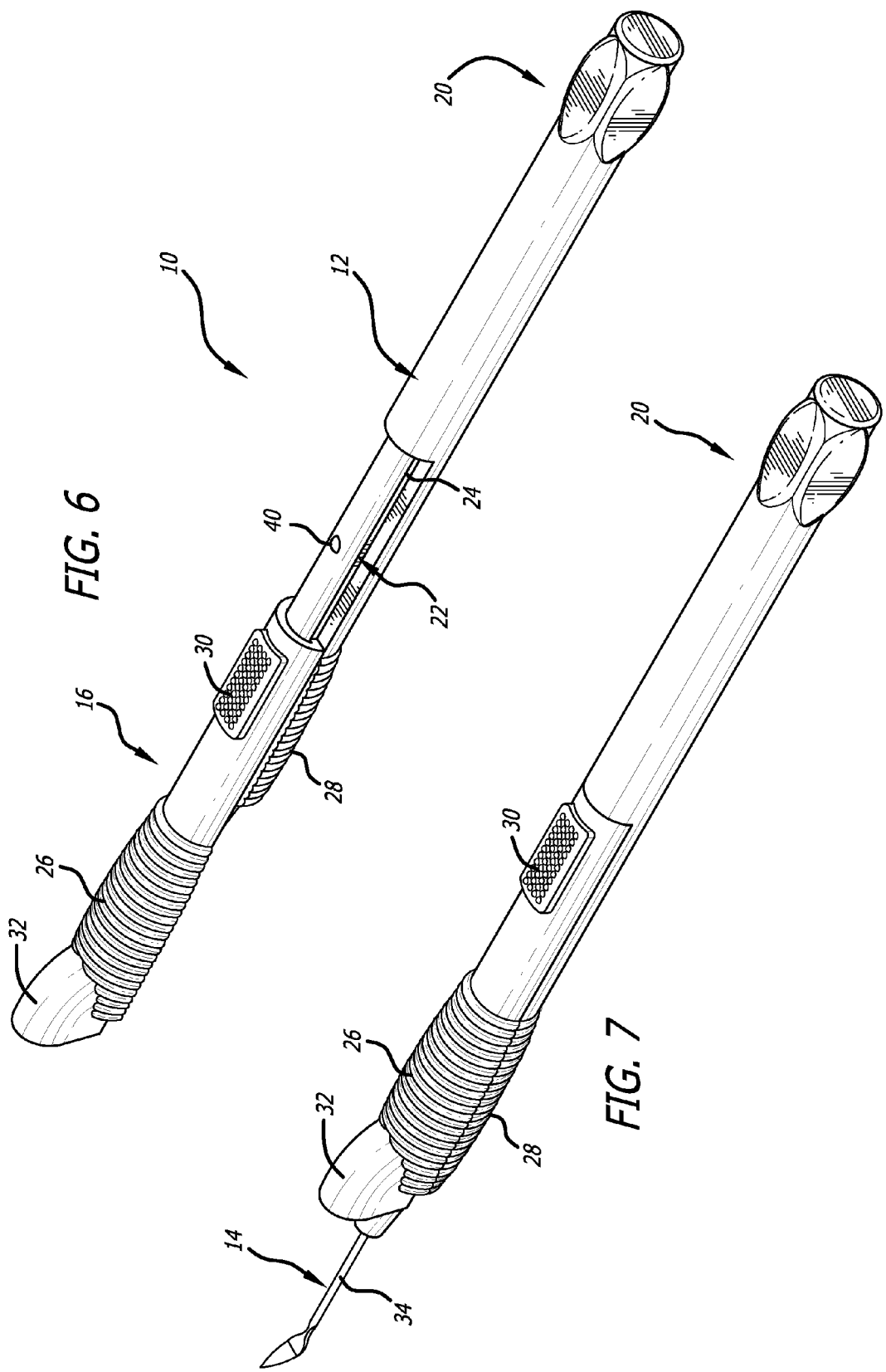

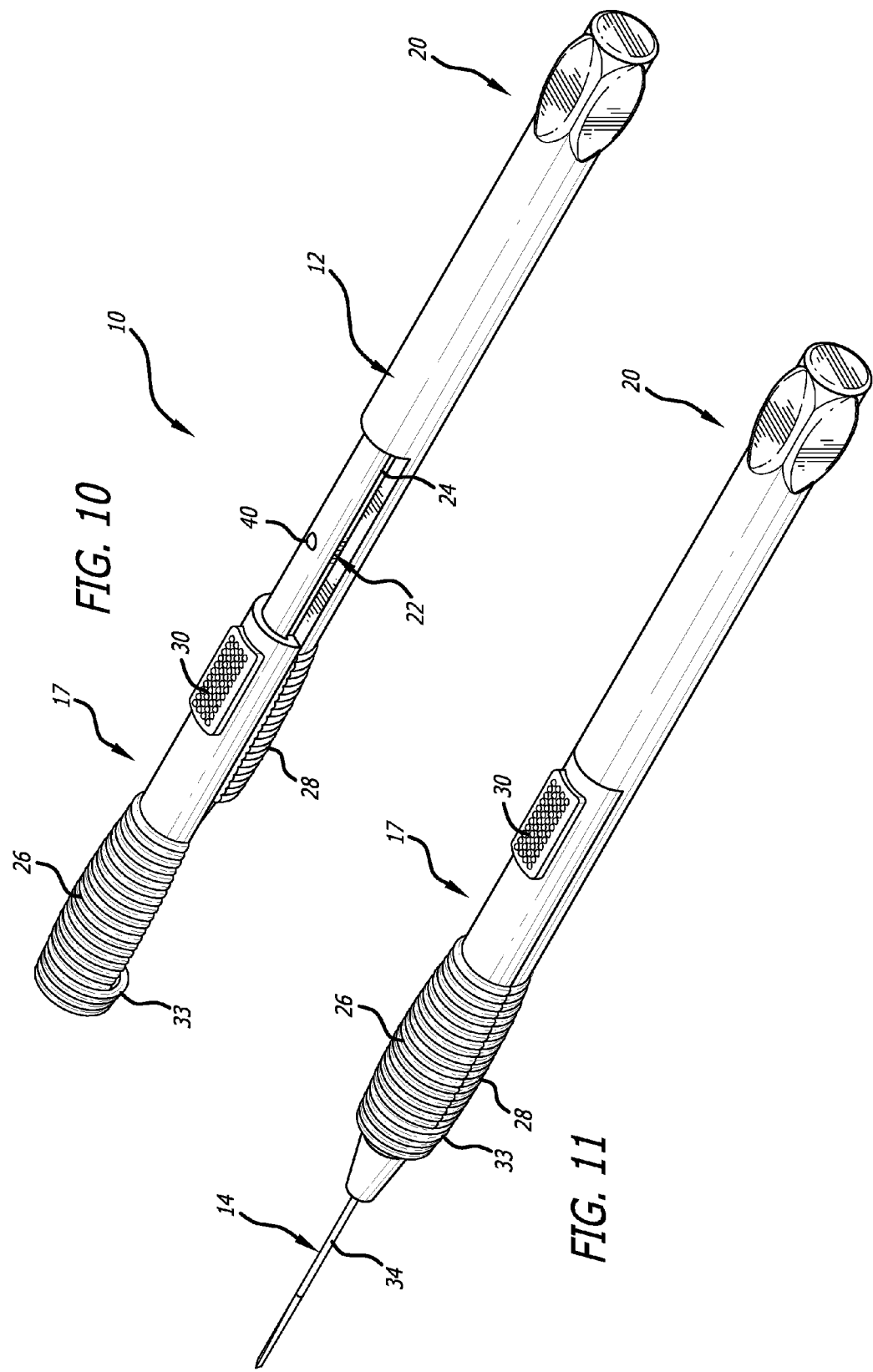

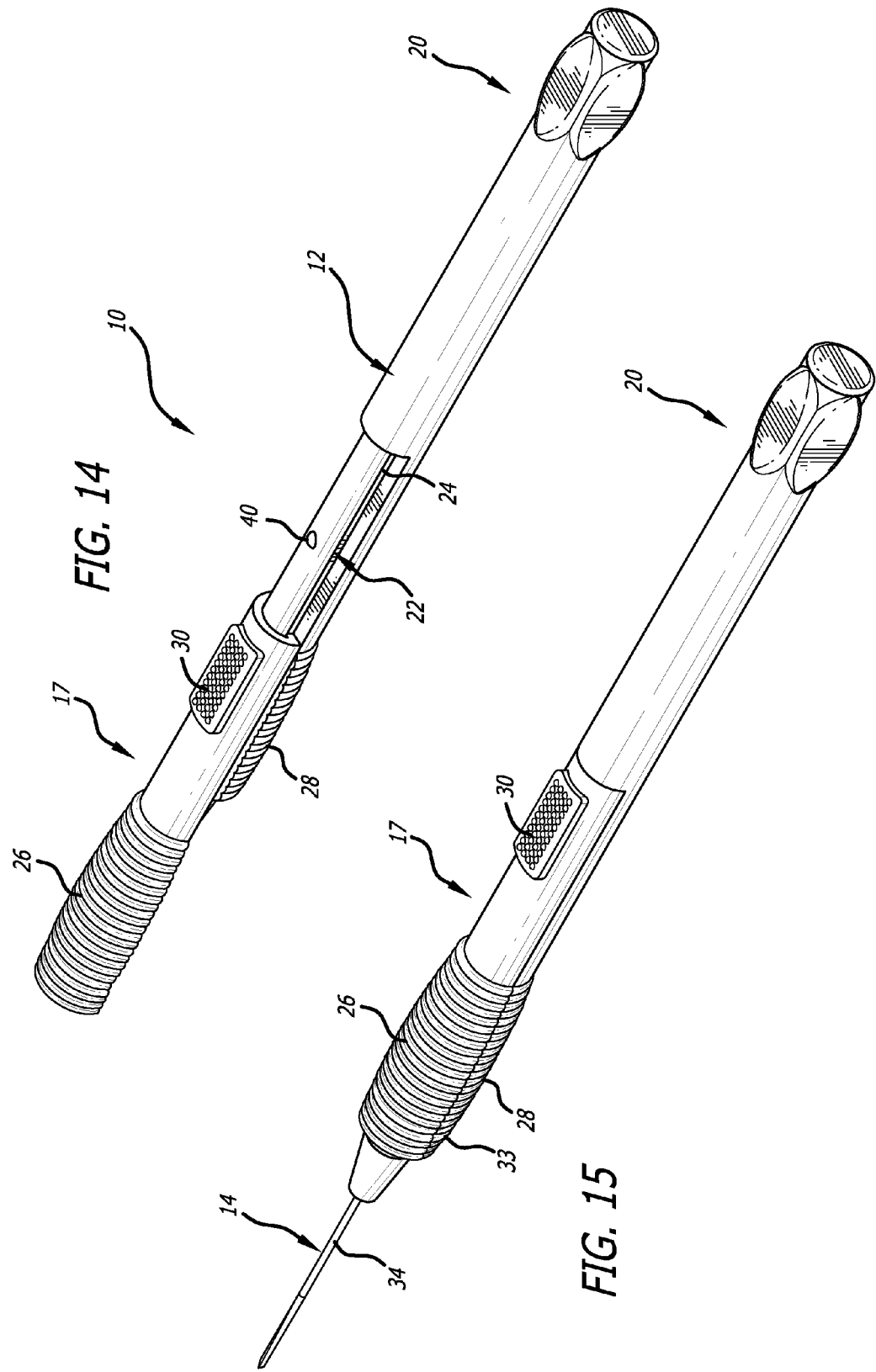

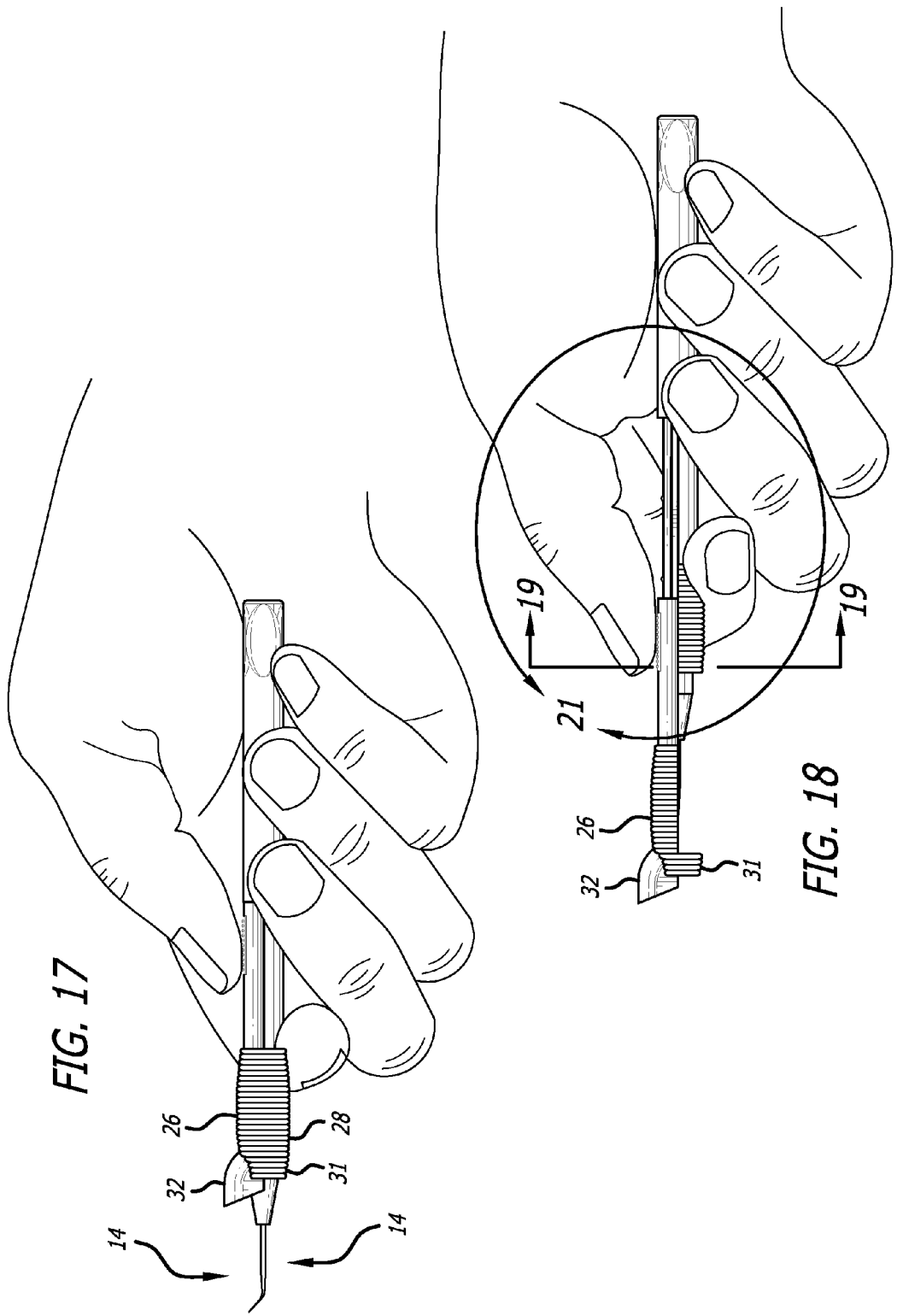

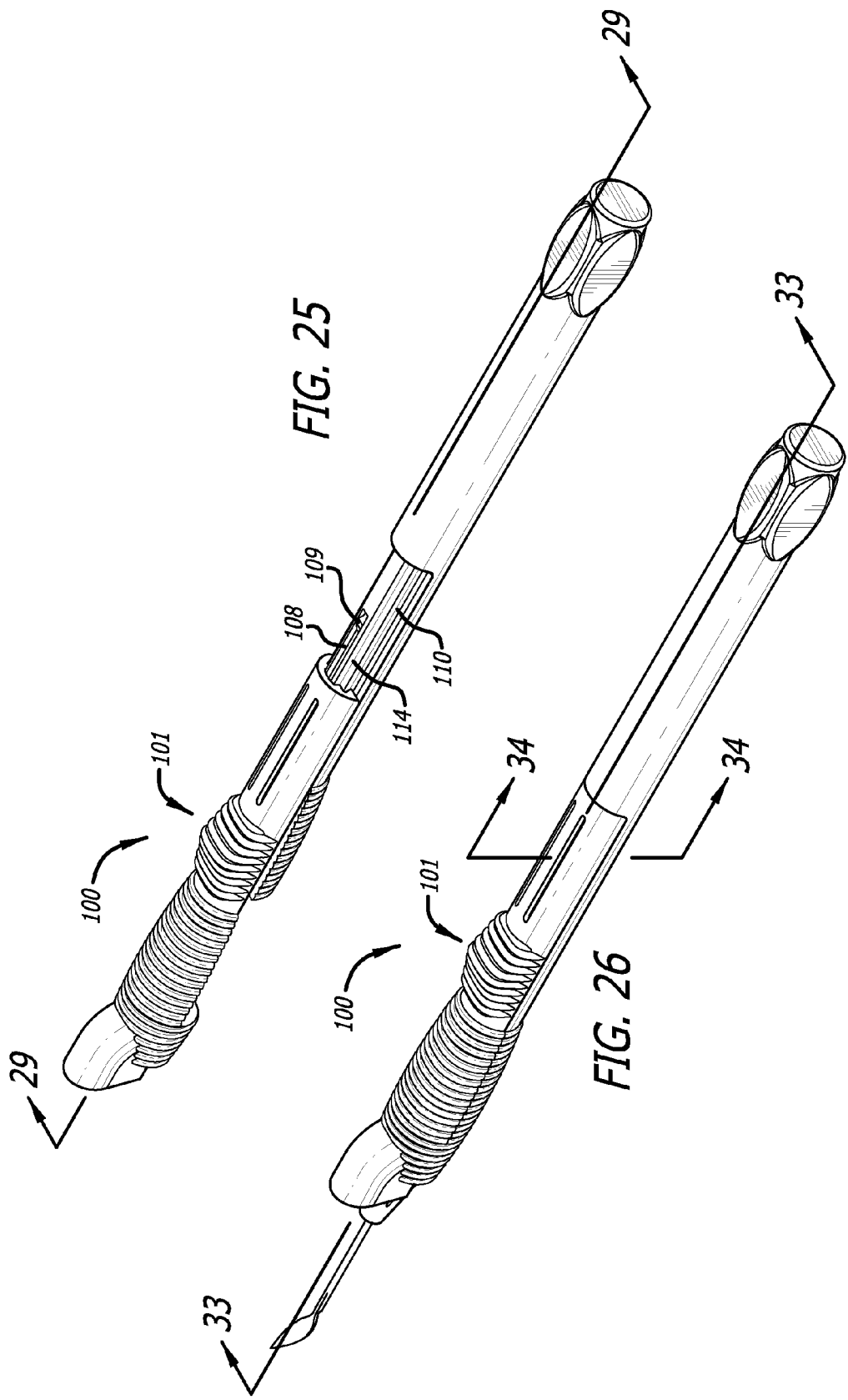

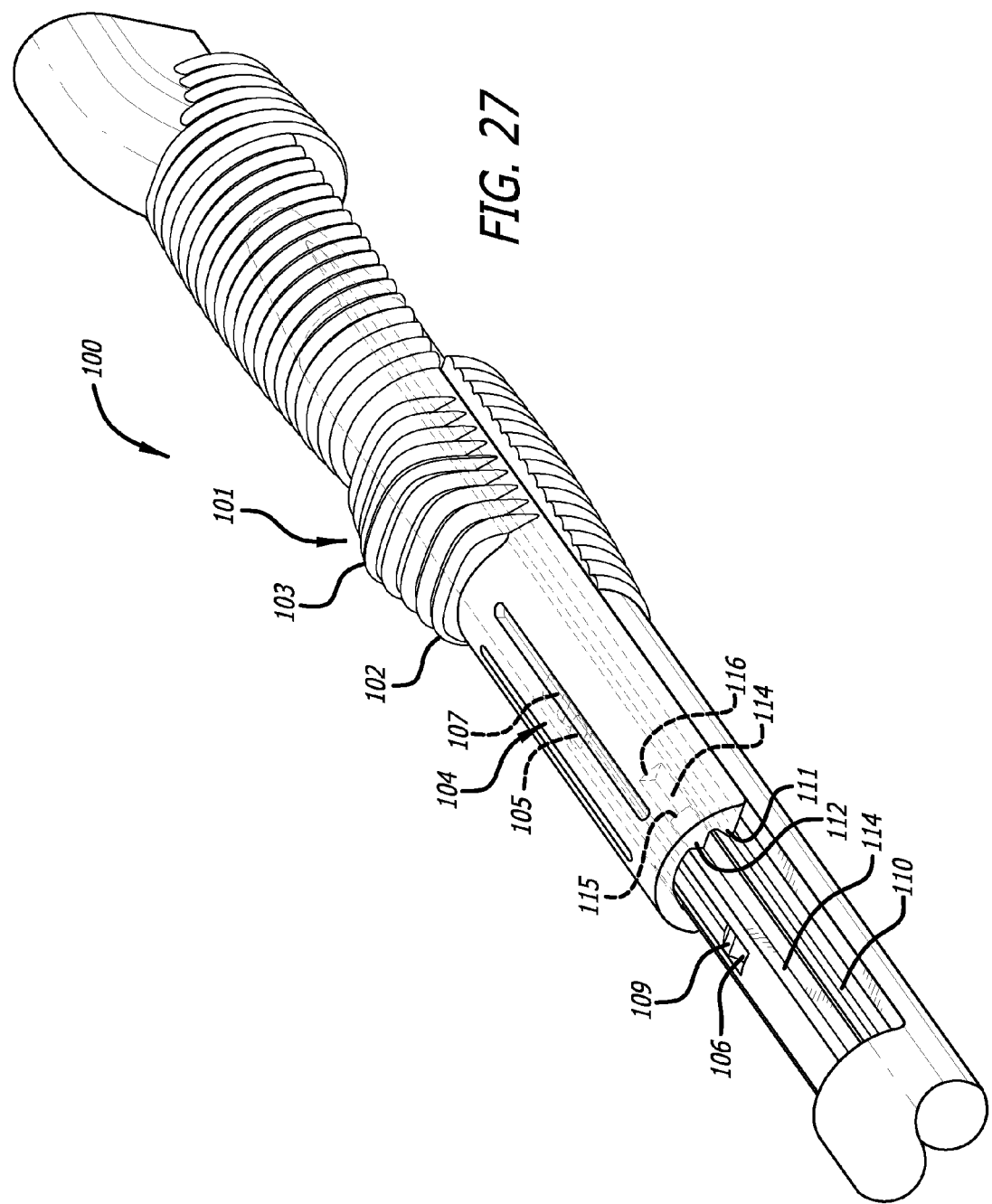

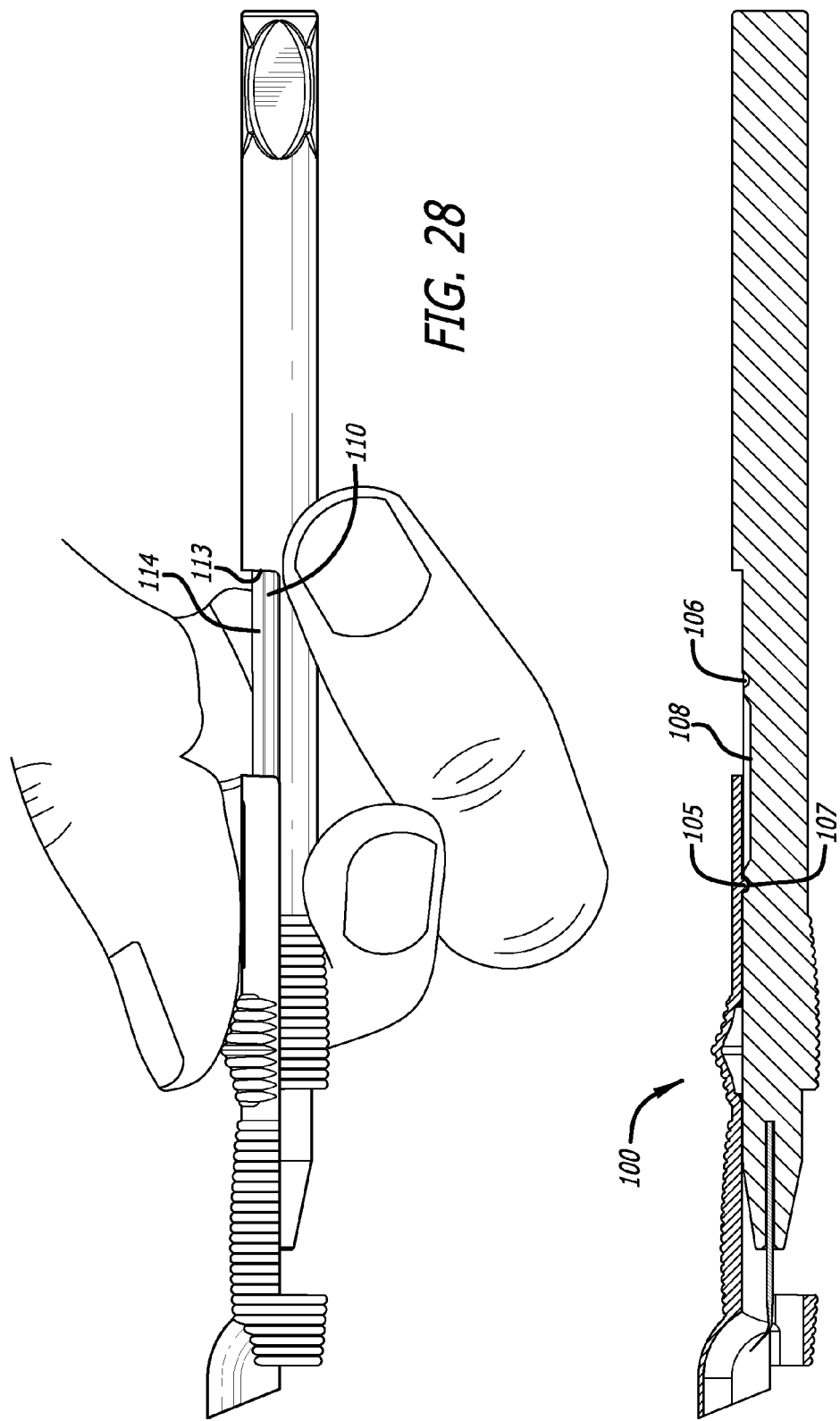

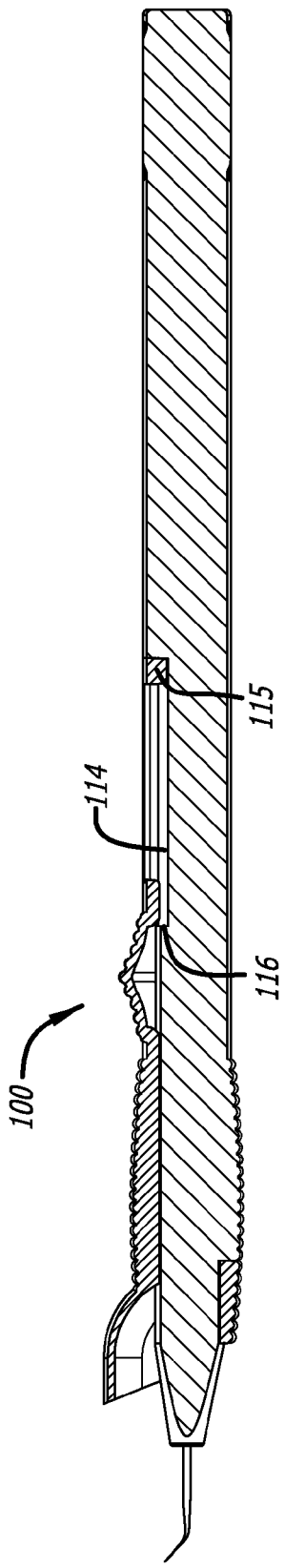
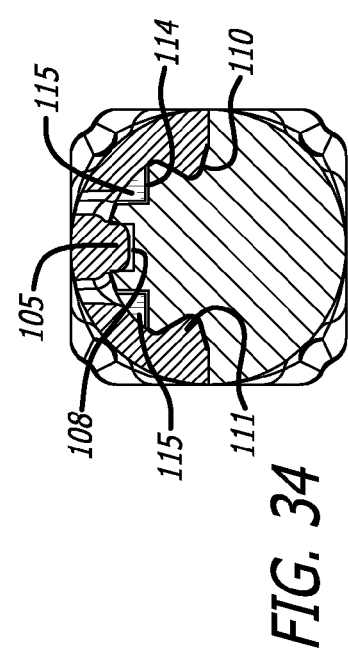
FIG. 33
FIG. 34

MICRO SURGICAL KNIFE WITH SAFETY FEATURE

RELATED APPLICATION

This application is a continuation in part of application Ser. No. 12/872,339 filed Aug. 31, 2010, entitled MICRO SURGICAL KNIFE WITH SAFETY FEATURE. This application relates to and claims priority from U.S. Provisional Application 61/322,784 filed Apr. 9, 2010, entitled MICRO SURGICAL KNIFE WITH SAFETY FEATURE and Design patent application Ser. No. 29/368,900 filed Aug. 31, 2010, entitled HANDLE FOR USE WITH A MICRO SURGICAL KNIFE, issued as U.S. Pat. No. D639,432 on Jun. 7, 2011. The contents of those applications are incorporated by reference herein in their entirety. The contents of these applications are incorporated by reference herein.

FIELD

The present disclosure relates to a surgical knife having a movable guard. In particular the knife is for ophthalmic applications.

In surgical procedures, the physician has to make an incision in the patient in order to remove unwanted tissue, repair damaged tissue, or implant a device to improve the patient's well being. In certain cases, all three of these activities, or a combination thereof, must be done in a single procedure.

Typically a nurse or other surgical assistant manages the devices that are used during delicate surgeries. With respect to scalpels, the nurse often hands the scalpel to the physician in a predetermined orientation so that the physician can grip the scalpel's handle without taking his or her eyes away from the patient. This also minimizes the possibility that the physician will be cut with the blade on the scalpel. After the physician completes the incision, the scalpel is handed back to the assistant for proper disposal or sterilization. If all appropriate protocols are followed, no hospital personnel will be cut by used or unused scalpel blades. Unfortunately, accidental cuts of hospital personnel do occur for a variety of reasons. For example, because the physician and assistant are concentrating on the patient and the procedure being performed on the patient, they may not pay close attention to the scalpels.

In view of the need for a scalpel that can at least minimize the chances of accidental cuts or nicks, while also protecting the cutting edge of the blade, numerous scalpels have been designed. These designs typically take the form of a scalpel having a guard that shields the sharp cutting surface of the blade from undesired contact with hospital personnel and surrounding surfaces. The guard in these devices can be extended to a position shielding the blade or retracted exposing the blade for use. Alternatively, the scalpel may be designed to allow the blade to move into or out of the scalpel handle, to either shield or expose the sharp cutting surface.

Unfortunately, these designs are deficient because they tend to be cumbersome, difficult to use, may cause unwanted shielding or exposure of the blade prior to the need for such shielding or exposure. Also, such devices may require considerable attention by the user to shield or expose the blade. Additionally, the shield may distort the handle outline when retracted, making the handle difficult to hold or control. Any design which allows the blade to move, for retraction or extension design purposes, also introduces concerns regarding exact blade positioning and rigidity during use. Such concerns also apply in cases in which the user is required to hold the retracted shield as a grip, allowing any movement between shield and handle to possibly result in unwanted movement of the blade.

Accordingly, a need exists for a device and method to provide a shielding mechanism that is simple to use and remains locked in a shielding position until disengaged by the user mechanism. The handle and shielding mechanism must also provide a uniform gripping surface when retracted, allowing user control of the scalpel without any unwanted gripping surface or blade movement.

SUMMARY

This disclosure provides a device that may be used to shield and protect a scalpel blade, and minimize the chances of cuts or nicks during handling or disposal. Further the device is easy to use and that can be operated by one hand of the user. Also the device will inhibit the shield to be accidentally displaced when fully extended and expose the blade.

The knife guard can be retracted to expose the blade when in use, and can be extended to cover the blade when not in use.

A surgical knife safety handle device comprises a handle body which is essentially a solid member having a distal end, a proximal end, and a longitudinal length of the body between the distal and proximal ends and without a hollow barrel extending from the distal to the proximal end of the body. The body has at least one formation extending on the outside of the body. There is a knife holder at the distal end of the handle body extending from the distal end. A movable guard engages with the formation for longitudinal movement between an extended position and a retracted position with respect to the handle body. The guard has a proximal end and a distal end for at least partially enclosing a knife blade attachable to the knife holder, and the guard is slidably mounted with the formation.

The device permits one handed operation. The guard or shroud can be extended or retracted with either hand. The mode of operation is apparent and an intuitive push/pull to extend or retract guard and thus does not require explanation or instruction. Moreover the device may be disassembled for cleaning as needed and thus can be reusable if needed. The guard is formed of a clear material with a low profile that does not interfere with vision in use, and thus reduces shadowing in the operative field.

The motion of the guard is essentially solely linear and not rotational or transverse relative to the longitudinal axis of the body. There is no spring member to secure the guard to the body, but the inherent inter-engaging frictional shapes of the two components, namely the integral body member and the guard member is sufficient to secure the guard and body together in its operative manner that is solely limited as a linear movement.

The engaging surface of a pad to effect movement of the guard is relatively large and in addition to the pad intended for finger or thumb use, the guard can be moved or pushed linearly by physical interaction by the finger or thumb anywhere on its outside surface of the guard.

Besides the knife itself, there are only two components necessary for the entire functional product and thus the manufacture and use of the product is easy and straightforward. Indeed assembly of the two components of body and guard is by a simple snap on action whereby the extremities on the guard are slightly expanded to fit into the cutout so that the ends of the guard engage slots in the cutout under frictional engagement as the ends snap into the slots under the inherent resilience or memory of the guard material.

Appropriate stops are added between the two members to regulate different positions of the two components relative to each other. Ideally the guard portion is semicircular relative to the circular body, and thus embraces the body over about 50 percent of its circumference.

In other forms the shroud is sufficiently lengthened to allow the addition of a leaf spring feature on the dorsal surface, although other shapes such as a half-cylinder could be employed. The spring has a hemispherical protrusion on its underside that engages with a slot on the handle. With a spring there is detent positive engagement and audible "click" when it seats.

The disclosure is further setout in the following detailed description.

DRAWINGS

The above and other objects and advantages will be apparent upon consideration of the following drawings and detailed description. The embodiments of the present disclosure are illustrated in the appended drawings in which like reference numerals refer to like elements and in which:

FIG. 2 is a perspective view of an embodiment of the present disclosure with the first form of the guard in an extended position to cover the blade;

FIG. 3 is a perspective view of an embodiment of the present disclosure with the first form of the guard in a retracted position to expose the blade;

FIG. 6 is a perspective view of an embodiment of the present disclosure with the second form of the guard in an extended position to cover the blade;

FIG. 7 is a perspective view of an embodiment of the present disclosure with the second form of the guard in a retracted position to expose the blade;

FIG. 10 is a perspective view of an embodiment of the present disclosure with the third form of the guard in an extended position to cover the blade;

FIG. 11 is a perspective view of an embodiment of the present disclosure with the third form of the guard in a retracted position to expose the blade;

FIG. 14 is a perspective view of an embodiment of the present disclosure with the fourth form of the guard in an extended position to cover the blade;

FIG. 15 is a perspective view of an embodiment of the present disclosure with the fourth form of the guard in a retracted position to expose the blade;

FIG. 17 is a side view of an embodiment of the present disclosure showing a hand operation with a guard in a retracted position to expose the blade;

FIG. 18 is a side view of an embodiment of the present disclosure showing a hand operation with a guard in an exposed position to cover the blade;

FIG. 25 is a perspective view of the other embodiment of the present disclosure with the first form of the guard in an extended position to cover the blade;

FIG. 26 is a perspective view of the other embodiment of the present disclosure with the first form of the guard in a retracted position to expose the blade;

FIG. 27 is a perspective view of the other embodiment of the present disclosure of the of the guard;

FIG. 28 is a side view of the other embodiment of the present disclosure showing a hand operation with a guard in an exposed position to cover the blade;

FIG. 29 is a detailed cross sectional side view on the center line and along line 29-29 of FIG. 25.

FIG. 33 is a detailed cross sectional side view off the center line and along line 33 -33 of FIG. 26.

FIG. 34 is a cross sectional end view though lines 34-34 of FIG. 26.

Figure 1:
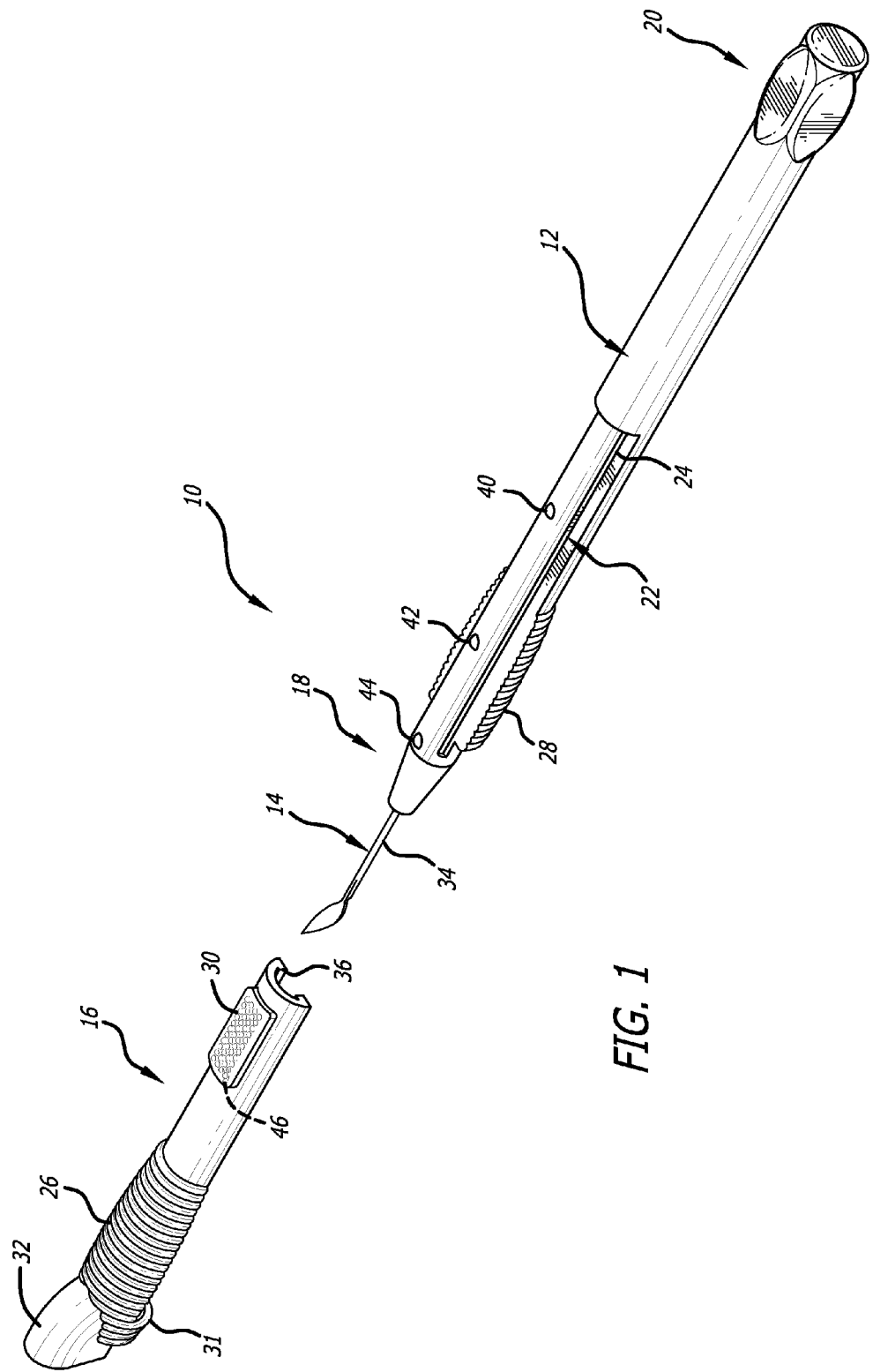
FIG. 1 is a perspective view of an embodiment of the present disclosure with one form of the guard in a removed separated and extended position to expose the blade.
Figure 4:
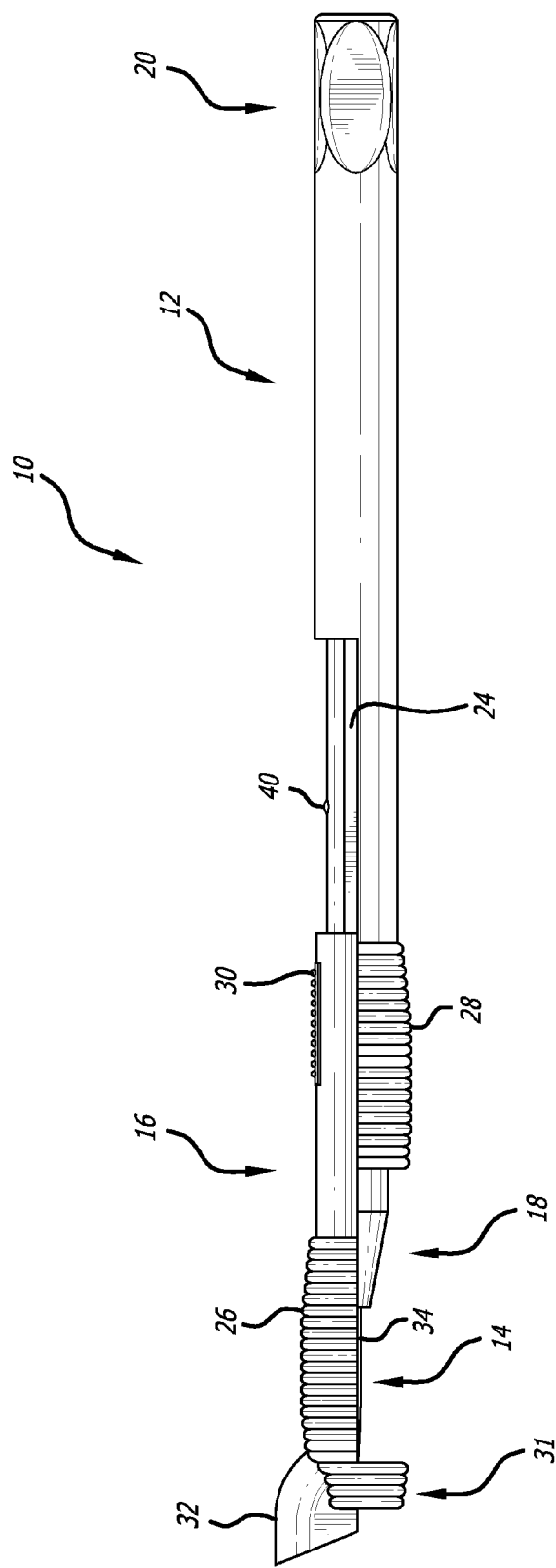
FIG. 4 is a side view of an embodiment of the present disclosure with the first form of the guard in an extended position to cover the blade.
Figure 5:
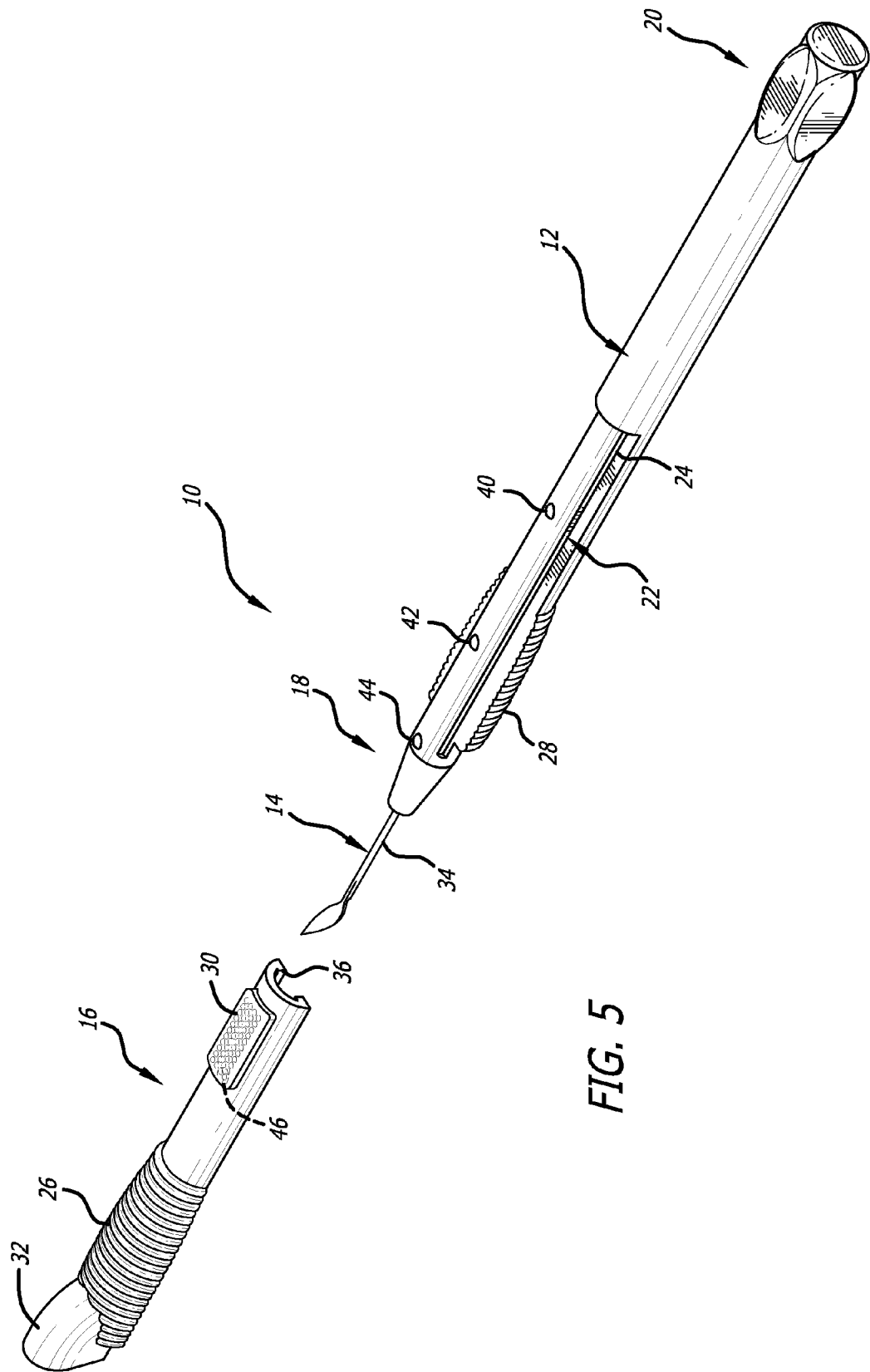
FIG. 5 is a perspective view of an embodiment of the present disclosure with a second form of the guard in a removed separated and extended position to expose the blade.
Figure 8:
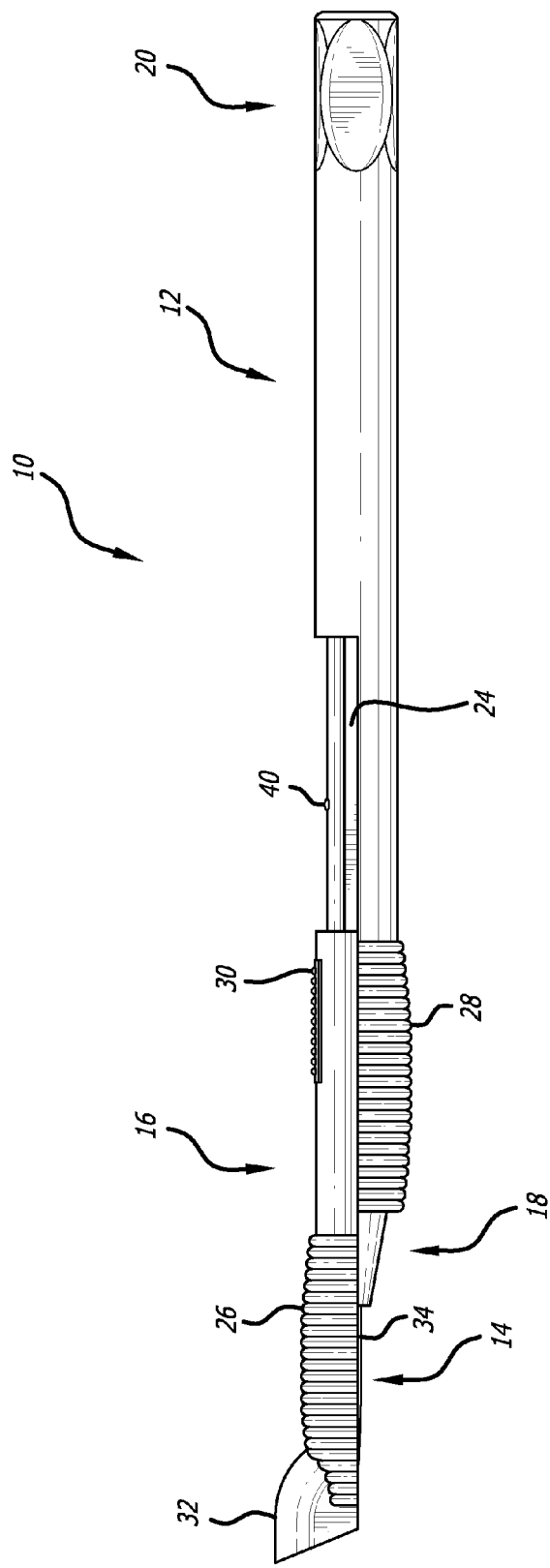
FIG. 8 is a side view of an embodiment of the present disclosure with the second form of the guard in an extended position to cover the blade.
Figure 9:
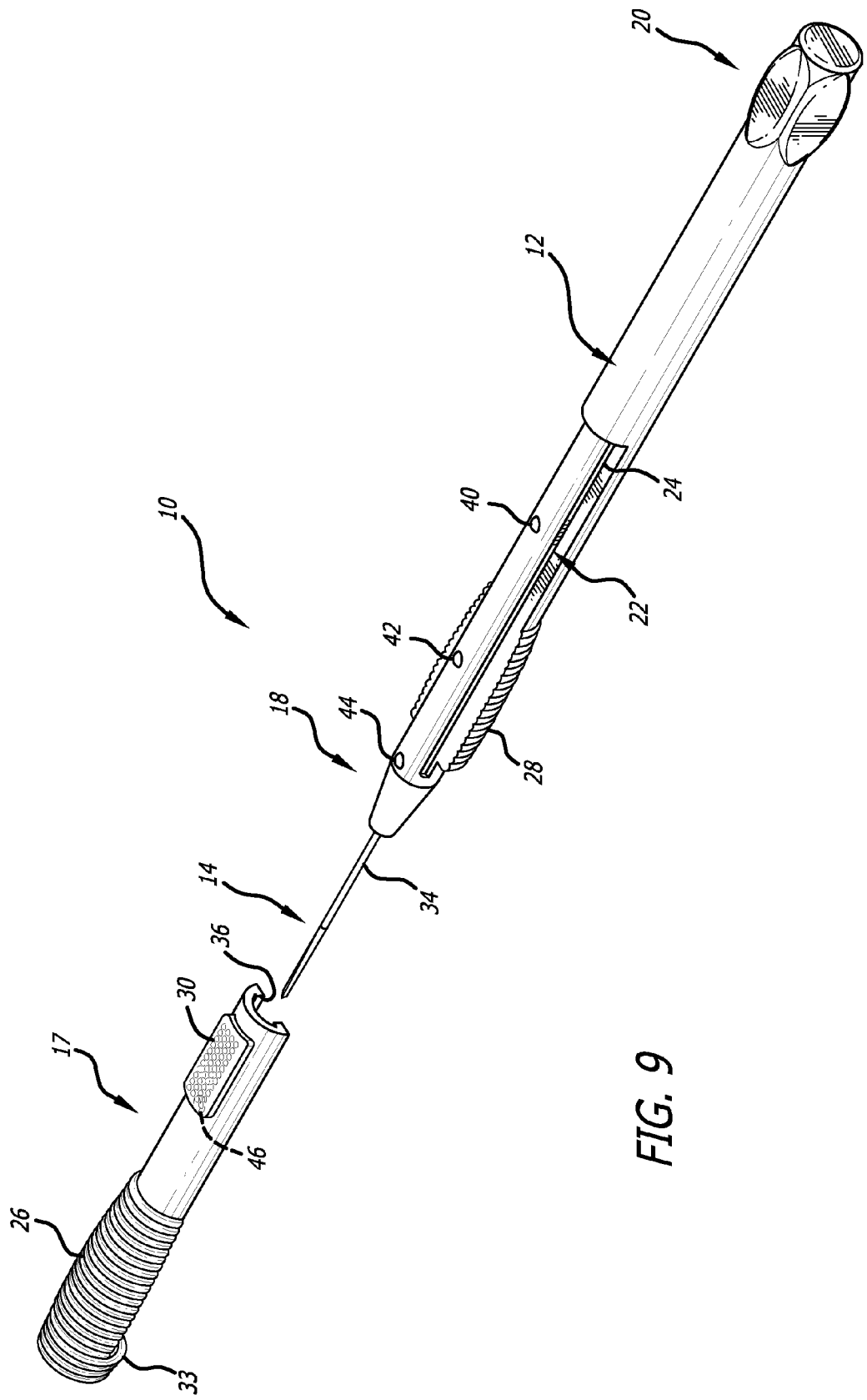
FIG. 9 is a perspective view of an embodiment of the present disclosure with a third form of the guard in a removed separated and extended position to expose the blade.
Figure 12:
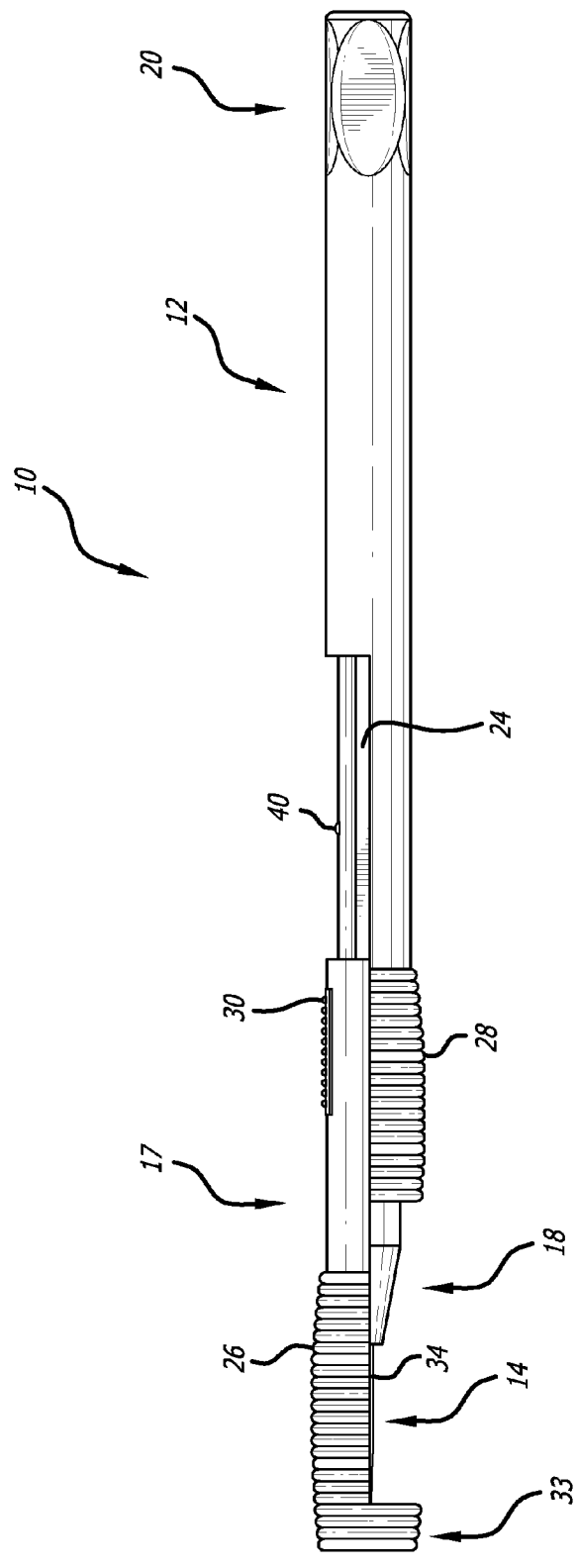
FIG. 12 is a side view of an embodiment of the present disclosure with the third form of the guard in an extended position to cover the blade.
Figure 13:
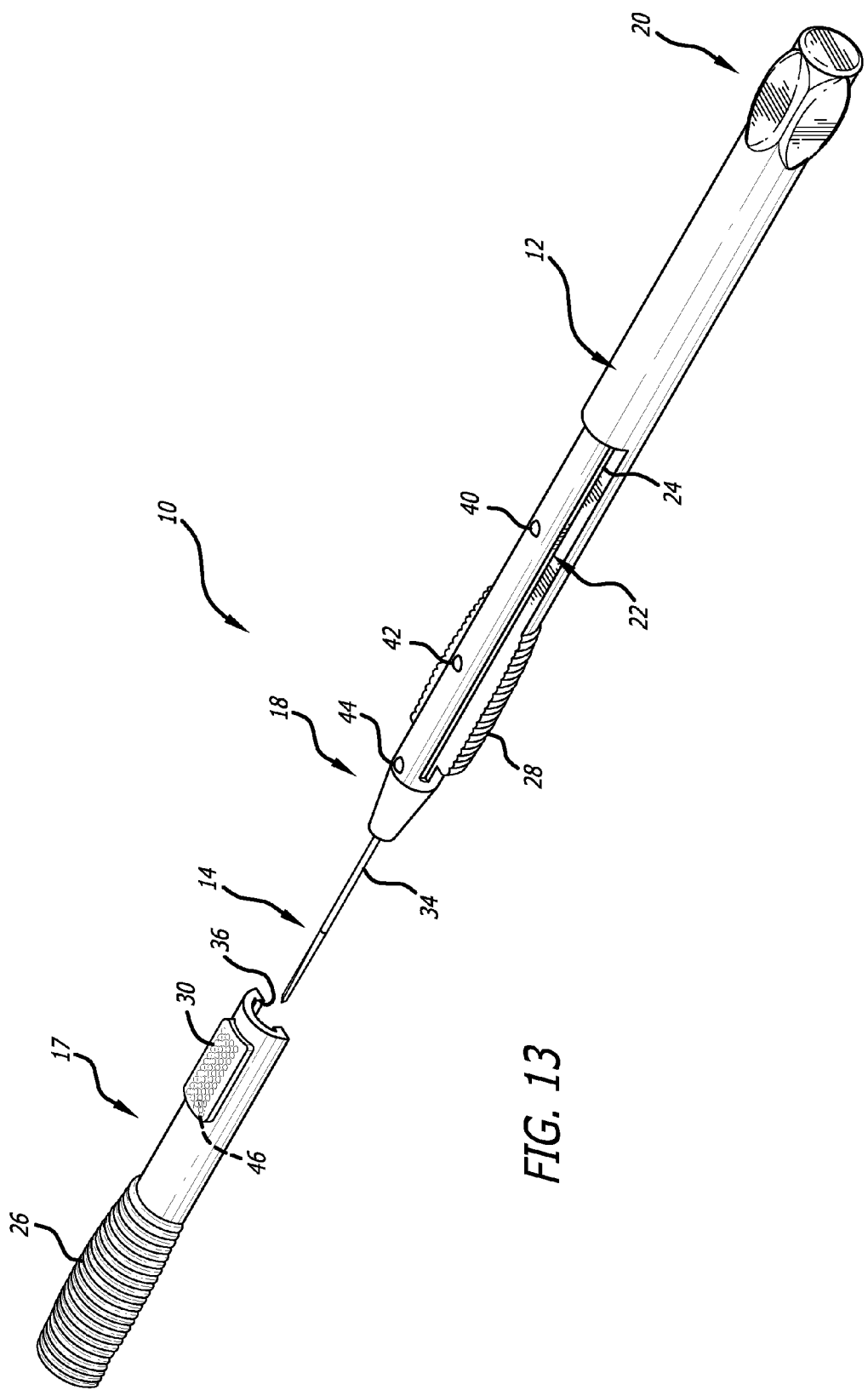
FIG. 13 is a perspective view of an embodiment of the present disclosure with a fourth form of the guard in a removed separated and extended position to expose the blade.
Figure 16:
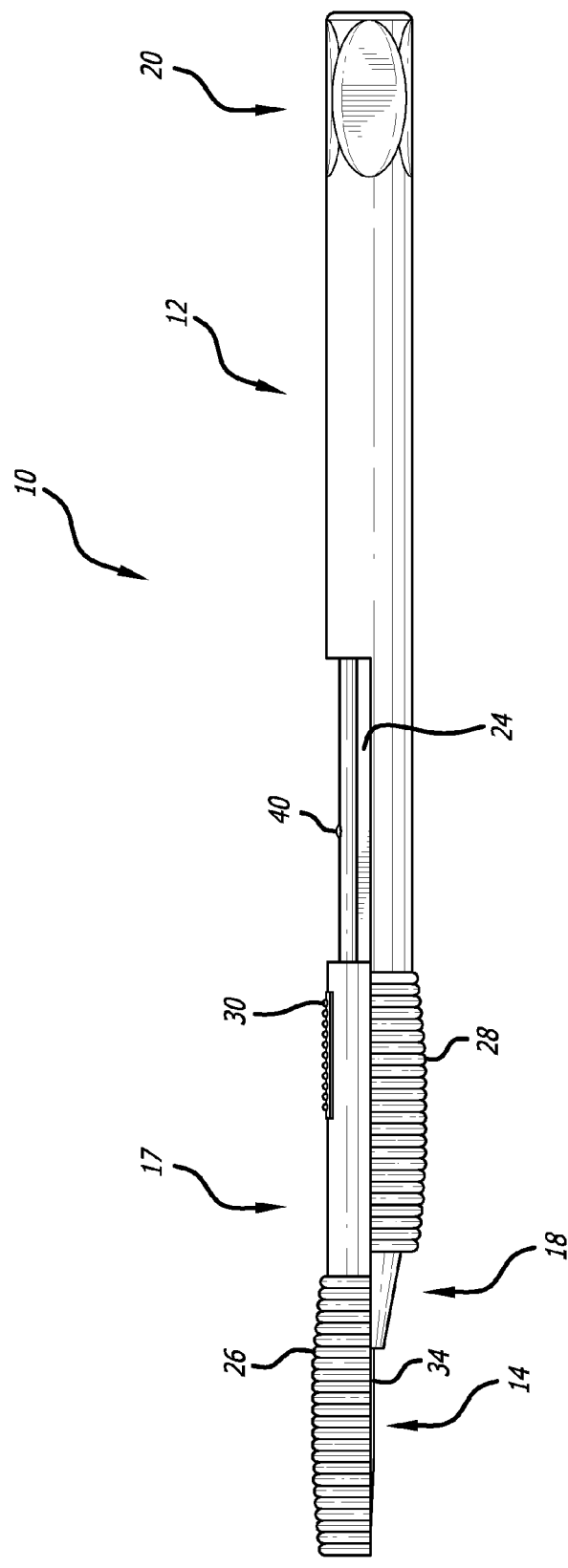
FIG. 16 is a side view of an embodiment of the present disclosure with the fourth form of the guard in an extended position to cover the blade.
Figure 19:
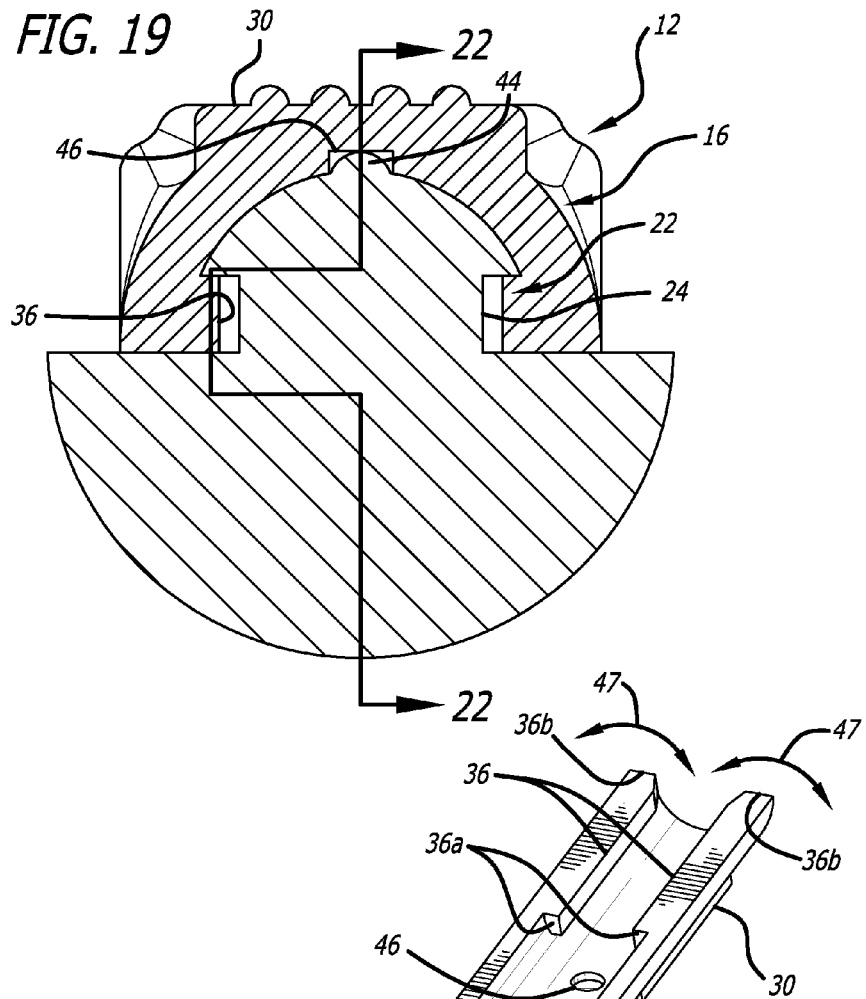
FIG. 19 is a cross sectional end view though lines 19-19 of FIG. 18.
Figure 20:
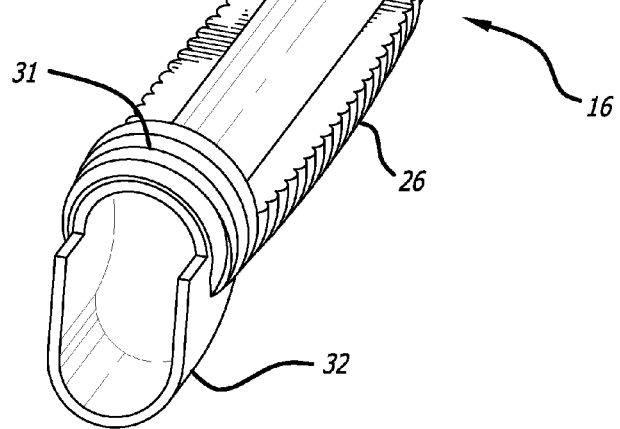
FIG. 20 is a perspective view of an embodiment of the present disclosure of the of the guard.
Figure 21:
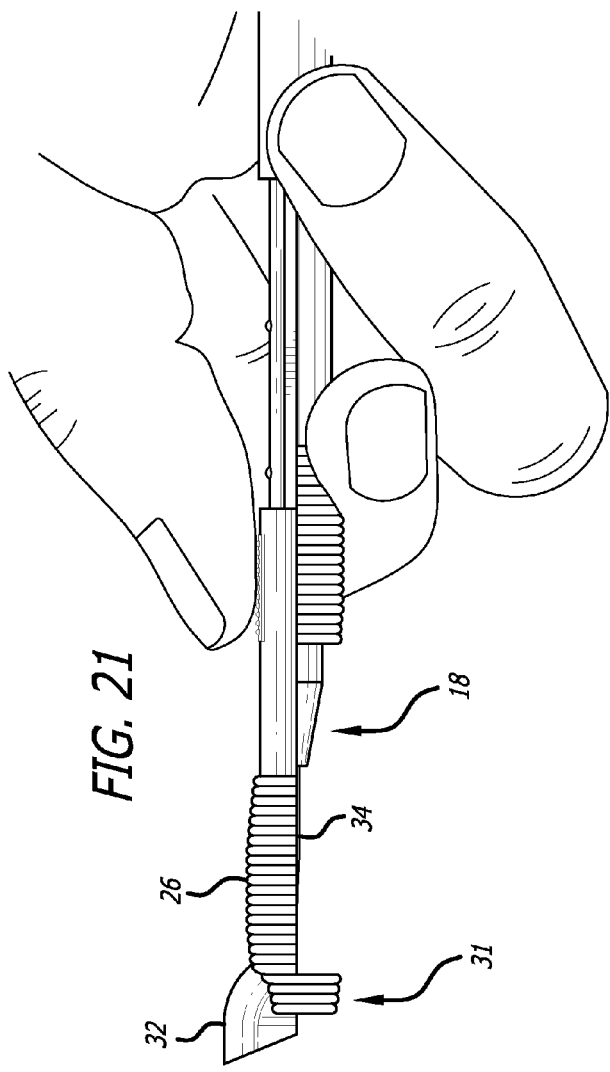
FIG. 21 is a side view of another embodiment of the present disclosure showing a hand operation with a guard in an exposed position to cover the blade.
Figure 22:
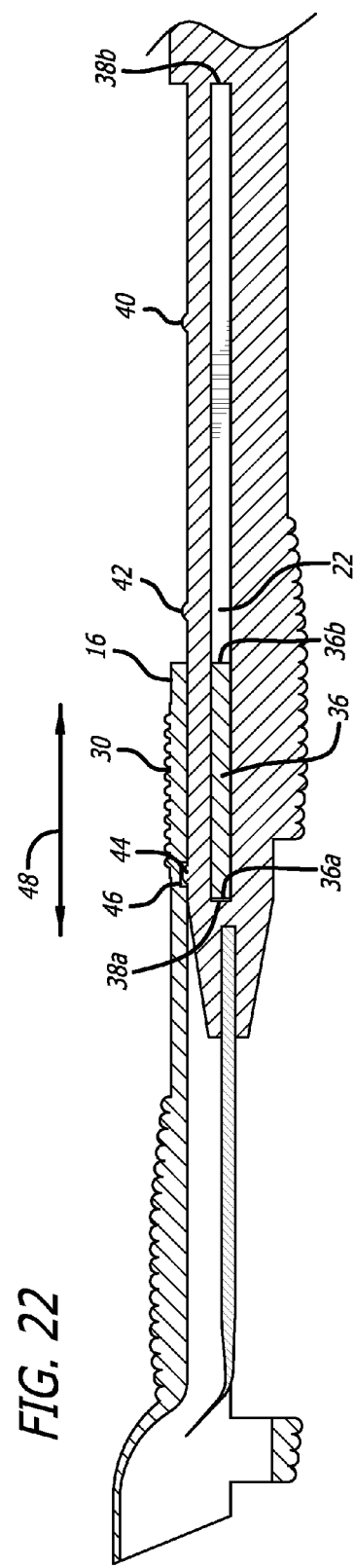
FIG. 22 is a detailed cross sectional side view along line 22-22 of FIG. 19.

The components in the figures are not necessarily to scale, emphasis instead being placed upon illustrating the principals of the disclosure.

Description

A surgical knife safety handle device comprises a handle body having a distal end, a proximal end, a longitudinal length of the body extending along a longitudinal axis between the distal and proximal ends. The body is essentially solid and has at least one slot extending on the outside of the body.

There is a knife holder at the distal end of the handle body for extending from the distal end. The knife holder is nonmovable longitudinally relative to and fixed to the distal end.

A movable guard engages with the slot for longitudinal movement between an extended position and a retracted position with respect to the handle body. The guard has a proximal end and a distal end for at least partially enclosing a knife blade attached to the knife holder.

The slot extends from the distal end to a predetermined position towards the proximal end, namely for part of the length of the body. The slot includes an end, the end acting to limit pushback of the guard from the distal end. The slot defines a length and the guard defines a length and the two lengths are substantially the same extent. The slot is defined in a cutout along a length of the body, and the guard defines a length and the lengths of the cutout, slot and guard are substantially the same extent.

There is also a second slot, spaced from the first slot, and both the slots are defined in the cutout along a length of the body and on either side of the cutout.

In one form, the guard includes an enlarged partially semicircular distal end connected with a semicircular guard body. In another form, the guard includes an enlarged at least partially circular distal end or circular portion or ring connected with a semicircular guard body.

The user control surface or pad can extend from the guard and it can include a ridged formation and may extend to, beyond or be indented relative to the general perimeter of the body.

The guard is located in a cutout in the body, and the guard is shaped to conform with an outward face essentially with the non-cutout portion of the body about and adjacent to the cutout portion. When the guard is retracted in the slot, the body and guard form a substantially consistent outward face around the body perimeter.

The guard includes a lip or spaced apart lips for engaging in the respective slot or spaced apart slots. The slots can take the form of other formations extending on the outside of the body. In some cases there may not be in a cutout in the body. The body may still have inter-engaging mating formations for engaging corresponding mating elements on the guard.

The movement of the guard relative to the body consists ideally of solely linear movement on the outside of the body relative to the longitudinal axis. There are detents between the body and guard. The solely linear movement of the guard relative to the body and the detent inter engagement regulates different relative longitudinal positions of the guard relative to the body. The guard may be relatively locked in position between or at the ends of the travel extremities of the guard relative to the body.

As used herein, the term "proximal" refers to a location on the surgical knife safety handle closest to the person using the device handle and farthest from the patient in connection with which the device handle is used. Conversely, the term "distal" refers to a location on the device handle of this disclosure farthest from the person using the device handle and closest to the patient in connection with which the device handle is used.

The surgical knife safety handle also includes a blade, knife or similar device, fixedly secured to the distal end of body. The guard is fixed can be slideably extended from the distal end of body to shield the exposed blade.

The embodiment of the present disclosure described discloses a micro surgical knife with a safety mechanism, for both ophthalmic and non-ophthalmic applications. The micro surgical knife 10 includes a body comprising a handle 12, a blade 14, and a guard 16. The blade 14 may be any suitable surgical blade made of, for example, stainless steel, titanium, ceramic, diamond or diamond-coated substrate, such blades being well-known in the art. The knife has a first and second end 18, 20 with a body extending there between. The blade 14 is fixed to the handle 12 at the first end, namely the distal end, 18 of the handle 12. The first end in a preferred embodiment is tapered to a smaller cross-section diameter, and can be, for instance, a point. The handle 12 has a cylindrical-like shape, similar to a pen or pencil, but may also have other shapes. For example, a contoured shape conforming to the user's grasp can be used.

The guard 16 is partially received within slots or channels 22 extending at least partly along the length of the handle 12 and rests in a surface cutout or indentation 24 and is axially aligned with the body. The guard or shroud 16 is adapted to be slidably moved, in a direction parallel to the length of the handle 12, between a retracted position and an extended position.

When the guard 16 is in the retracted position, it fills the surface indentation 24 to form an uninterrupted handle surface. The outer surface 17 of the guard comprises a ribbed patterned surface 26 which provides a gripping surface to assist the user in holding and using the knife 10 and sliding the guard 16. The body of the knife has a similar ribbed patterned surface 28, which corresponds to the ribbed patterned surface of the guard. When the guard 16 is in the retracted position, the ribbed patterned surfaces 26, 28 of both the guard and the body create a uninterrupted 360° ribbed patterned surface to provide a user a gripping surface to grip the knife. The outer surface of the guard further comprises a raised ridge textured surface 30 which is at an opposite end to a raised blade cover 32 of the guard. The raised ridged surface 30 provides the user with a roughened surface which allows the user to interchangeably slide the guard 16 between the retracted and extended positions.

With the guard 16 in an extended position, the raised blade cover 32 of the guard 16 covers the blade 14. The raised blade cover 32 and portion 31 or portion 33 of the guard 16 covers the blade 14 when the guard 16 has been moved into the extended position. The raised blade cover 32 can be adapted to cover various different shapes and sizes of blades 14, such as but not limited to, long blades, short blades or wide blades, etc. The raised blade cover 32 of the guard 16 provides a protective shell around the sharp edges of the blade, while the non-sharp edges of the blade, such as the stem 34 extending out from the pointed tip of the body and the first end 18 of the handle 12, are not covered and remain exposed.

The body of the knife comprises slots, grooves or channels 22, axially aligned with the body, which receive ribs or extensions 36 on the guard 16. The grooves 22 provide a pathway to guide the guard 16 in sliding movement between the retracted and extended positions. The guard 16 has a lip or rib 36 along each of its edges that engage with the corresponding groove 22 of the handle such that the handle receives each of the lips or ribs 36 of the guard 16. The ribs 36 are capable of traversing through the grooves 22 of the body to slidably move the guard 16 between the extended and retracted positions. The grooves 22 of the body do not extend the entire length of the body and terminate at a location proximate the first end 18 of the body to ensure that the guard 16 does not become detached from the handle 12.

The knife 10 further comprises a system whereby the guard has hard end stops. As such the ends 36a of the lips 36 would engage ends 38a of the slots at the extended position of the guard 16, and the ends 36b of the lips 36 would engage ends 38b of the slots at the retracted position of the guard 16.

Also the guard 16 can be maintained in either the extended or retracted position, until the user manually repositions the guard 16 to the alternate position. There are intermediate locations to secure the guard in intermediate positions as needed.

A first rounded indent 40 in the surface of the handle 12 provides a locking mechanism which holds the guard 16 in the retracted position when a raised pin 42 on a concave surface, opposite the ribbed pattern surface 28 and the raised dimpled surface 30 of the guard 16, engages the first rounded indent 44 in the surface of the handle 12. The handle 12 also has a second rounded indent 44 in the surface of handle 12 proximate to the first end 18 of the knife 10.

The second rounded indent 44 engages the recess 46 on the concave surface of the guard 16 to maintain the guard 16 in the extended position. In other embodiments, the body has additional projections and indents to accommodate different size blades and/or to prevent the guard 16 from becoming detached from the body. In further embodiments the indents 40, 44 can be projections projecting from surface which engage a plurality of depression in the matching surface to maintain the guard in the extended or the retracted position. The projections and depressions are not limited to rounded shapes. The projections and depressions can be in the form of a variety of shapes, such as but not limited to, quadrilaterals, triangular, and other polygonal shapes.

In yet other embodiments, the projection can comprise an irregular shape such that the projection has a vertical edge and a sloped edge, wherein the projection engages a correspondingly configured depression, such that the vertical edge of the projection engages the vertical edge of the depression to lock the guard in the extended or retracted position.

The projections engage with the depressions to lock the guard in the retracted position and in the extended position.

The surgical knife safety handle includes a body having a guard slideably received partially within body for longitudinal sliding movement between a retracted and extended position. The guard, when in the retracted position, forms a smooth, uninterrupted handle surface between distal and proximal ends, which is preferred by users of such devices when in use. Additionally, the enlarged guard portion, external to body when fully retracted, defines a partially semicircular contour about the area of the distal end and/or the knife holding portion of the surgical knife safety handle which gives the user better control and allows easier blade orientation during use.

The distal end of the guard also includes an outer surface having a ribbed, ridged or dimpled texture, extending from the distal end. The textured surface is sufficient to provide the user with a nonslip grip during use, and is duplicated in a similar position on the lower body contour wall such that when assembled, the textured surface appears uniform about an outside diameter of the body near the distal end. Although a textured ring ridged surface is shown in the embodiments, any nonslip surface can be used. Additionally, the nonslip surface can be extended or modified from the area shown and described.

The distal end of the guard further includes a semicircular mating part, extending rearward from the distal end, and providing a position in which the raised contoured surface of the exposed portion of the guard is seated when fully retracted. In the fully retracted position, the mating port and exposed guard portion of the guard are configured to provide the smooth, uninterrupted handle surface and essentially circular contour about the distal end, with the partially semi circular hood portion of the guard raised above the generally circular profile of the body and engaging guard.

The outside walls of the handle body define a substantially solid body without a chamber, and the distal end is the knife holder portion and has an axial aperture for receiving the shank of a knife.

The guard does not have a fully circular cross section at the distal end and this ensures the user is allowed to firmly grip a surface that is singularly molded with the blade holder. This presents a more positive grip which is less susceptible to unwanted blade or gripping surface movements due to tolerances between the guard and the body. The enlarged distal end of the guard which remains external to the body when fully retracted however is rigid enough to provide additional control and blade orientation with one or more fingers of the user if so desired during use.

The guard positioning surface has a generally flat face pad and is sized to fit on the surface of the guard. The guard flat face 30 is frictionally engaged by the finger or thumb of a user to direct and control guard travel between a fully extended and fully retracted position. The combined length of the surface 30 and guard is sufficient to allow a substantial portion of the guard to retract within body. Only a partial radius of the enlarged distal end of the guard remains exposed.

The guard extends between a generally circular cross section at a proximal end, and a generally semicircular cross section at an enlarged distal end. The guard is not fully circular along its entire length due to the need to surround the molded attachment of the holder and the blade, which is in rigid attachment to the body. The guard includes opposite engagement and shielding ends. At the engagement, or proximal end, the guard has a generally semi-circular cross section and is sized to slidably fit with the cutout in the body, and the mechanical frictional engaging surface 30 directs and controls the travel of the guard between a fully extended and fully retracted position.

The shielding, or distal end of the guard, has a generally semicircular cross section and is sized to extend and retract relative to the body. An enlarged partially semicircular area is provided at the extreme end of the distal end of the guard to provide adequate clearance of the blade when the guard is fully extended. Additionally, the enlarged partially semicircular area at the extreme distal end of the guard remains external to the body profile when the guard is fully retracted, and is rigid enough to provide additional control and blade orientation with one or more fingers of the user if so desired.

There is an anti-travel engagement between the guard and the body. When engaged and fully extended, additional movement of the guard is inhibited or resisted by the anti-travel mechanism of the coupling mechanism components.

A fully circular guard or ring may also be used to shield the exposed blade. The guard is fully circular at the distal end, which allows a larger portion of the guard to remain exposed when fully retracted. With the guard in a retracted position there is exposure of a knife or blade for use. The guard, when in the retracted position, forms an essentially smooth, uninterrupted handle surface between distal and proximal ends. When not in use, the guard can be extended to safely shield the blade.

A handle body defines a substantially solid body. Additionally, the outer circumference surface area of an exposed portion of guard also includes a ridged texture, such that when fully retracted, the texture surface area is unbroken about the distal end of the body.

The cutout, slots and rails on the guard serve to provide a slidable engagement surface for the guard to travel between fully extended and fully retracted positions. The guard can include a fully circular distal end, provided to shield the blade when fully extended. Opposite ends of the guard provide respectively first and second lips for engaging the first and second slots in the cutout. The slots 24 are provided to engage the lips 36.

The engaging surface 30 of a pad to effect movement of the guard is relatively large and in addition to the pad intended for finger or thumb use, the guard can be moved or pushed linearly as indicated by arrow 48 by physical interaction by the finger or thumb anywhere on its outside surface of the guard. Assembly of the two components of body and guard is by a simple snap on action whereby the extremities of the lips 36 on the guard are slightly expanded to fit into the cutout so that the ends of the guard 16 engage slots 24 in the cutout under frictional engagement as the lips 36 snap into the slots 24 under the inherent resilience or memory of the guard material. This action is indicated by arrows 47.

Various guards could be fabricated to fit outside the body and the handle and still achieve the desired coverage of the blade. By disposing the guard on the outside the device and having a cutout in the body, the handle or body of the device can be constructed with a matching diameter with the guard, or allow for the guard to better shield the blades described above or other blade geometry.

The guards could further comprise various shapes which can provide blade shielding at various places or of various strengths. Specifically, different guard shapes may provide different strength characteristics, and further allow the guard to withstand higher forces. These may also allow for a smaller guard, or enlarged guard distal end, thereby minimizing visual interference with the blade while providing maximum protection from blade contact. The guard and enlarged guard distal end can be either open or closed, and can achieve full circumference protection or provide alternative means to shield a blade depending on blade design. A partially or fully semi-circular guard, or the guard and enlarged guard distal end can still include other shapes, such as, but not limited to, triangle, square and/or box shapes, and still other shapes having multiple facets or sides, all with or without a circular or radius cross section, but which still provide shielding for blades of different geometry.

The blade shielding device of the present disclosure can withstand an inadvertent force. Such protection can be provided by utilizing a locking feature, for instance additional detents. These embodiments do not disengage or allow the guard to move from the shielding state to the non-shielding state by any reasonable inadvertent force applied longitudinally to the guard.

The device of the disclosure can be constructed of any suitable material, including a number of materials which can be autoclaved for repeated use. For example, where the embodiments are provided with metal blades and suitable body materials, multiple uses are possible using steam autoclave processes. A preferred blade material includes stainless steel (for metal spring versions only), and the body and guard can be constructed of polyamide. The guard can be constructed of transparent or opaque polycarbonate.

Where repeated use is not desired, other blade materials can be provided, including silicon, and the body can be constructed of autoclave intolerant materials, such as high impact polystyrene. The use of high impact polystyrene will result in the substantial destruction of the device when autoclaved, thereby preventing reuse. In such applications, the guard can be constructed of polyetherimide and polycarbonate, respectively.

Figure 23:
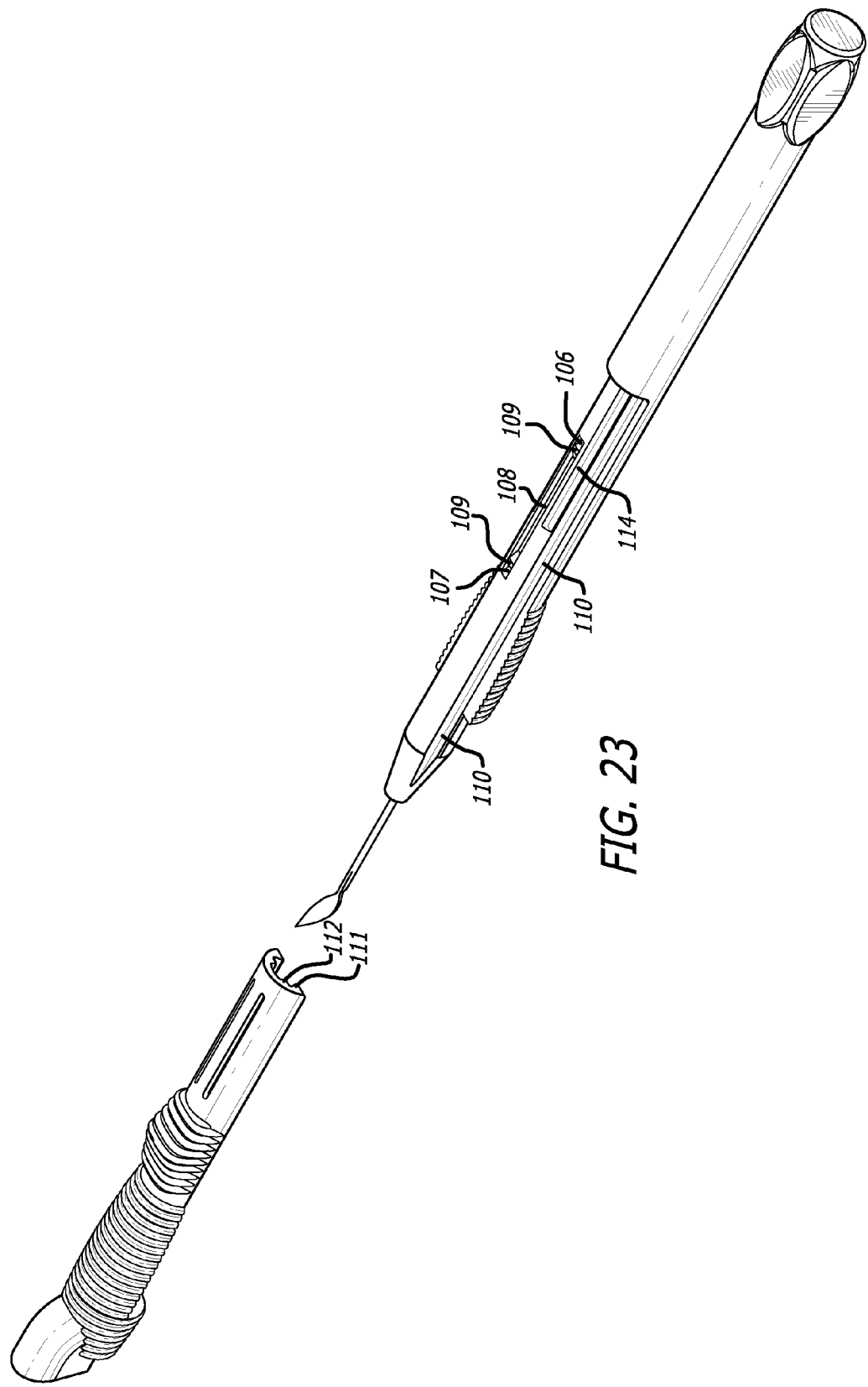
FIG. 23 is a perspective view of another embodiment of the present disclosure with one form of the guard in a removed separated and extended position to expose the blade.
Figure 24:
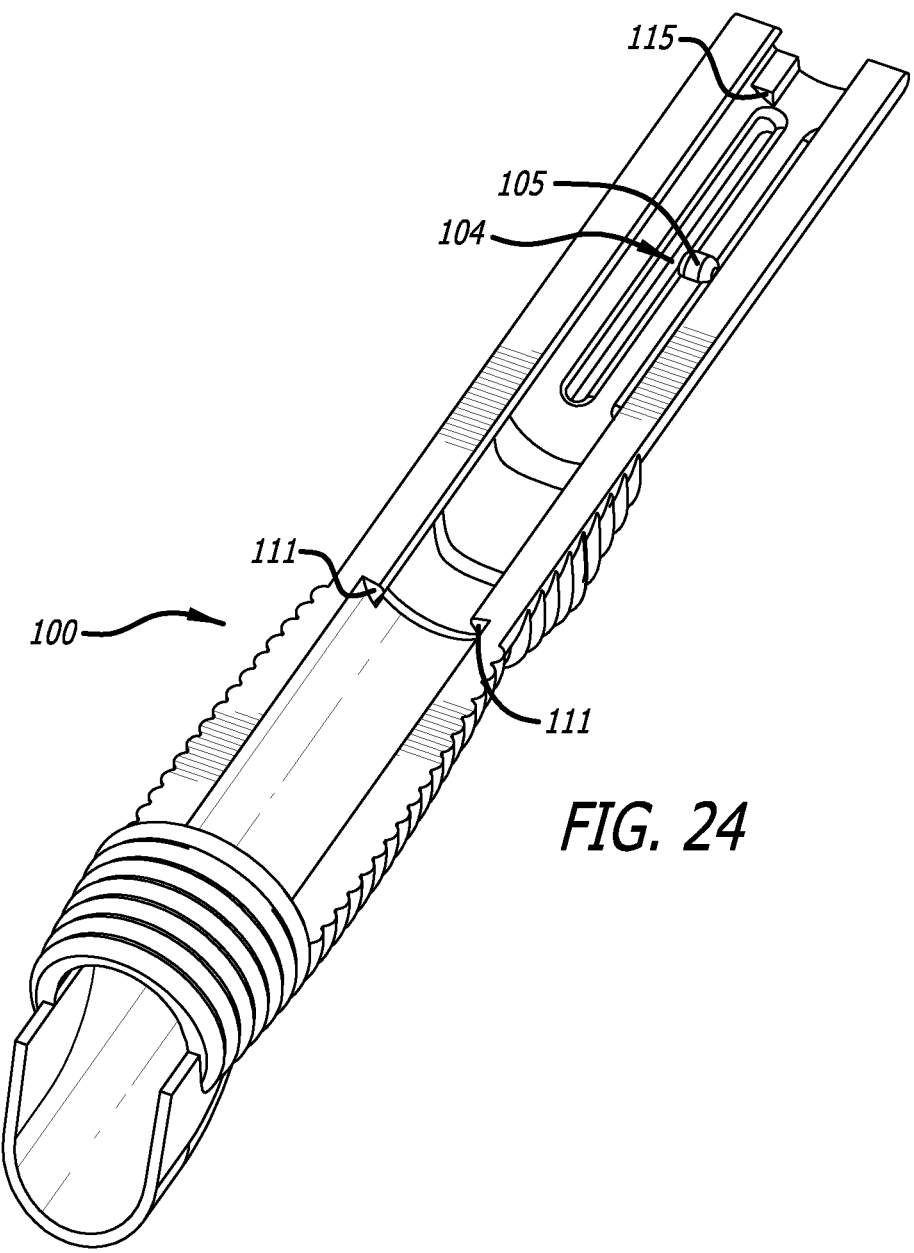
FIG. 24 is an under view in perspective of the guard or shroud of the other embodiment.
Figure 30:
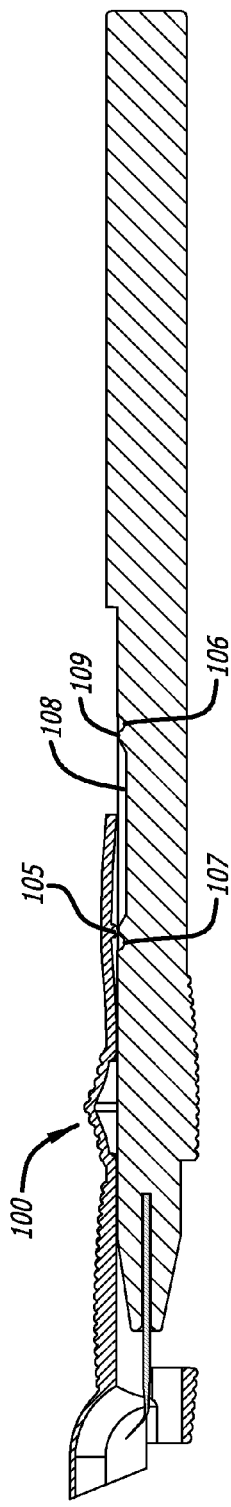
FIG. 30 is a cross sectional side view of the other embodiment of the present disclosure showing operation with a guard in a slightly deformed position when the guard has moved from the full coverage position from over the blade.
Figure 31:
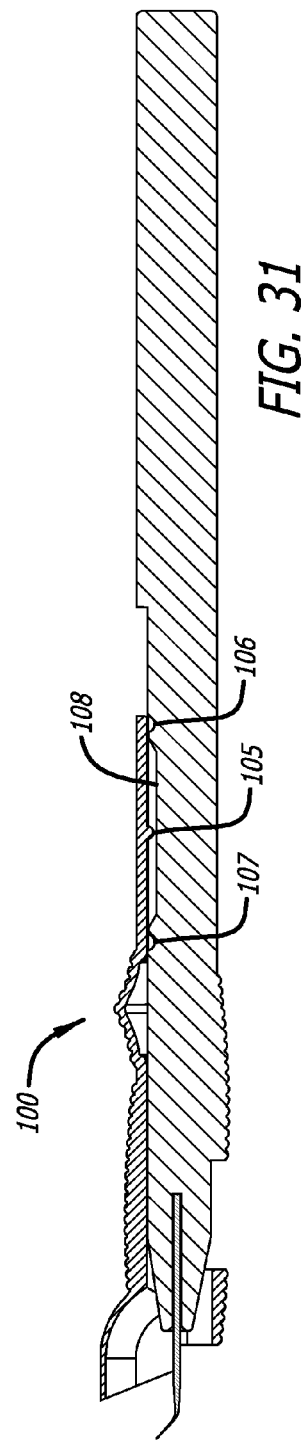
FIG. 31 is a cross sectional side view of the other embodiment of the present disclosure showing operation with a guard in a reformed normal position when the guard has moved further into the retracted position away from the full coverage position from over the blade.
Figure 32:
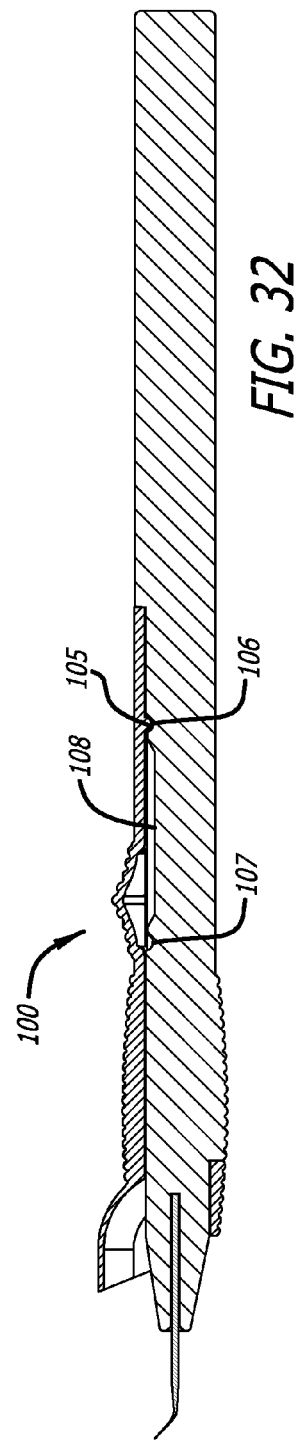
FIG. 32 is a cross sectional side view of the other embodiment of the present disclosure showing operation with a guard in a reformed normal position when the guard has moved further into the fully retracted position away from the full coverage position from over the blade.

In another embodiment as illustrated in FIGS. 23 to 34, the guard includes a latch, the latch including a leaf spring with a knob on the undersurface of the guard. The knob is for engaging a detent depression in a channel on the handle body. There are multiple longitudinal channels in the top surface of the handle. The channels are for engaging with mating multiple longitudinal protrusions under the guard thereby to hinder it from sliding off. The protrusions are located in respective positions removed from the side ends of the guard. The spring includes a protrusion on its underside for engaging with a slot on the handle. There are two longitudinal grooves in the handle, the grooves straddling the detent recess and engaging tabs on the proximal end of the guard. This provides a positive stop whereby the shroud is hindered from sliding off the end of the handle to expose the blade.

The guard or shroud 100 includes a thumb button 101 is located more towards the end of the shroud and its profile 102 is extended in a broadly triangular profile form as seen in cross section along its length, or is such that there is high point 103, for instance at about the center of the button 101, the center being between the front and back of its length. As such, the button 101 gives a different traction for moving the shroud 100.

There is a latch 104 which is defined as a leaf spring and includes a small knob 105 on the underside of the shroud 100. The end of the knob 105 engages detent depression 106 towards the distal end or depression 107 towards the proximal end of handle. These detents or depressions 106 and 107 are formed respectively in a channel 108 on the handle. When in either the distal or proximal depressions there is positive engagement of the shroud on the handle. There may be some slight deformity or relative movement of the shroud 100 relative to the slot 108 in the handle as the shroud moves between retracted and extend positions and crosses the threshold of the top 109. This achieves a positive positioning of the shroud relative to the handle and creates a "clicking" sound when the shroud 100 is moved from a position of rest in either direction. This gives the user of the knife a sense of feeling and an audible indication of the position of the shroud 100 relative to the handle when the shroud moves from its normal position, namely when the knob being a substantial hemispherical type protrusion 105, namely having an arcuate or curved surface, moves over the top 109 of the barrier in the slot 108. When the knob 105 and the barrier are in position abutting each other so that the ends engage, the guard is deformed as when the knob is in similar end to end engagement top of the wall of the detent or depression 107. As such when the knob enters or leaves the depression, the guard shape is changed There are two additional channels 110 formed in the handle top surface on either side of the top of the handle. These channels 110 engage with two mating protrusions 111 under the shroud 100 to hinder the shroud 100 from sliding off the handle. The end wall 112 of the shroud 100 provides in the withdrawn position a positive stop by engaging the end wall 113 formed in the distal end of the overall groove in the handle. In the second position where the shroud 100 covers the blade of the knife as shown in FIG. 27, there is an internal stop which rides in slot 114 and the internal wall 115 engages the detent end wall 116 positively.

This further embodiment is different from the prior embodiments as follows:

1. The thumb grip on the shroud is moved to a position proximal to the ribbed feature. The grip is more prominent and ribs improve traction. The grip is in a comfortable position and the added traction facilitates actuation.

2. The shroud is lengthened about ¼" relative to the first embodiment and this allows the addition of a leaf spring feature on the dorsal surface. The spring has a small hemispherical protrusion on its underside that engages with a slot on the handle. The spring gives a positive detent engagement with and audible "click" when it seats.

3. The recess in the handle is lengthened ¼" to accommodate the longer shroud. A recess with detents at the retracted and extended shroud positions are on the handle dorsal surface.

4. Two longitudinal grooves straddle the detent recess and engage tabs on the proximal end of the shroud. They provide a positive stop so that the shroud should not slide off the end of the handle to expose the blade.

This embodiment separates the shroud retention, detent, and positive stop functions.

Although only a few exemplary embodiments of the present disclosure have been described in detail above, those skilled in the art will readily appreciate that many modifications are possible in the exemplary embodiments without materially departing from the novel teachings and advantages of this disclosure. The present disclosure is described herein with reference to certain embodiments, but it is understood that the disclosure can be embodied in many different forms and should not be construed as limited to the embodiments set forth herein.

Accordingly, all such modifications are intended to be included within the scope of this disclosure as defined in the following claims.

The invention claimed is:

1. A surgical knife comprising:

A handle body having a reduced portion and a full portion, a top surface of the reduced portion is offset below a top surface of the full portion, the reduced portion top surface having an elongated slot with at least one detent, the reduced portion having two side channels that are substantially parallel with the elongated slot, a blade holder fixed to a distal end of the reduced portion of the handle body, a blade received in the blade holder, a guard having an upper surface and a lower surface defining a space, the lower surface of the guard having two projections, the upper surface of the guard having two through slots defining a leaf spring, a knob extending from the leaf spring into the space, and a user control surface spaced from the two through slots, wherein the two projections of the guard are movably received in the two side channels of the reduced portion and the reduced portion is received in the space so that the lower surface of the guard engages the reduced portion top surface and the knob is movably received in the elongated slot, wherein the guard is movable between an extended position where the guard covers the blade and a working position where the blade is exposed and the guard upper surface is substantially flush with the top surface of the full portion, and the knob engages the at least one detent in the slot to keep the guard in the extended position or in the working position.

2. The surgical knife of claim 1 further comprising: the full portion of the handle body having a distal wall that engages proximal ends of both of the two side channels and acts as a stop for the guard when the guard moves from the extended position to the working position.

3. The surgical knife of claim 1 further comprising: the at least one detent in the elongated slot is two detents in the elongated slot wherein the knob engages one of the detents to keep the guard the working position and the knob engages the other of the detents to keep the guard in the extended position.

4. The surgical knife of claim 1 further comprising: the user control surface is a ridged formation that extends beyond a perimeter of the upper surface of the guard.

5. The surgical knife of claim 1 further comprising: a distal end of the guard includes a gripping portion and the distal end of the reduced portion includes a gripping portion.

6. The surgical knife of claim 5 further comprising: the guard gripping portion incorporates ribs and the reduced portion gripping portion incorporates rib, and wherein when the guard is in the working position, all of the ribs are substantially aligned.

7. The surgical knife of claim 1 further comprising: the guard upper surface and the full portion top surface are curved surfaces wherein the shape of the surgical knife is substantially cylindrical.

8. The surgical knife of claim 1 further comprising: the reduced portion top surface is a curved surface, the guard lower surface is curved surface, and the space is a concave space.

* * * * *